United States Patent
Libbus et al.

(10) Patent No.: US 8,396,560 B2
(45) Date of Patent: Mar. 12, 2013

(54) SYSTEM AND METHOD FOR CLOSED-LOOP NEURAL STIMULATION

(75) Inventors: Imad Libbus, St. Paul, MN (US); Andrew P. Kramer, Stillwater, MN (US); Julia Moffitt, St. Anthony, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 1809 days.

(21) Appl. No.: 10/992,319

(22) Filed: Nov. 18, 2004

(65) Prior Publication Data

US 2006/0106429 A1    May 18, 2006

(51) Int. Cl.
*A61N 1/18* (2006.01)

(52) U.S. Cl. .................. 607/48; 607/37; 607/44

(58) Field of Classification Search .................. 607/44, 607/117, 48, 37
See application file for complete search history.

(56) References Cited

U.S. PATENT DOCUMENTS

| | | | |
|---|---|---|---|
| 4,201,219 A | 5/1980 | Bozal Gonzalez |
| 4,791,931 A | 12/1988 | Slate |
| 5,111,815 A | 5/1992 | Mower |
| 5,190,035 A | 3/1993 | Salo et al. |
| 5,199,428 A | 4/1993 | Obel et al. |
| 5,203,326 A | 4/1993 | Collins |
| 5,243,980 A | 9/1993 | Mehra |
| 5,318,592 A | 6/1994 | Schaldach |
| 5,324,316 A | 6/1994 | Schulman et al. |
| 5,330,507 A | 7/1994 | Schwartz |
| 5,356,425 A | 10/1994 | Bardy et al. |
| 5,411,531 A | 5/1995 | Hill et al. |
| 5,437,285 A | 8/1995 | Verrier et al. |
| 5,507,784 A | 4/1996 | Hill et al. |
| 5,522,854 A | 6/1996 | Ideker et al. |
| 5,540,730 A | 7/1996 | Terry, Jr. et al. |
| 5,578,061 A | 11/1996 | Stroetmann et al. |
| 5,658,318 A | 8/1997 | Stroetmann et al. |

(Continued)

FOREIGN PATENT DOCUMENTS

| EP | 0481583 A2 | 4/1992 |
|---|---|---|
| EP | 0688578 A1 | 12/1995 |

(Continued)

OTHER PUBLICATIONS

"International Search Report for Application No. PCT/US2005/042009, Date mailed Mar. 27, 2006", 12 pages.

(Continued)

*Primary Examiner* — Niketa Patel
*Assistant Examiner* — Alyssa M Alter
(74) *Attorney, Agent, or Firm* — Schwegman Lundberg & Woessner, P.A.

(57) ABSTRACT

Various aspects of the present subject matter provide a device. In various embodiments, the device comprises a port adapted to connect a lead, a pulse generator connected to the port and adapted to provide a neural stimulation signal to the lead, and a signal processing module connected to the port and adapted to receive and process a nerve traffic signal from the lead into a signal indicative of the nerve traffic. The device includes a controller connected to the pulse generator and the signal processing module. The controller is adapted to implement a stimulation protocol to provide the neural stimulation signal with desired neural stimulation parameters based on the signal indicative of the nerve traffic. Other aspects are provided herein.

33 Claims, 15 Drawing Sheets

U.S. PATENT DOCUMENTS

| | | | |
|---|---|---|---|
| 5,690,681 | A | 11/1997 | Geddes et al. |
| 5,700,282 | A | 12/1997 | Zabara |
| 5,913,882 | A | 6/1999 | King |
| 5,916,239 | A | 6/1999 | Geddes et al. |
| 6,006,134 | A | 12/1999 | Hill et al. |
| 6,058,331 | A | 5/2000 | King |
| 6,073,048 | A * | 6/2000 | Kieval et al. ............... 607/17 |
| 6,134,470 | A | 10/2000 | Hartlaub |
| 6,161,042 | A | 12/2000 | Hartley et al. |
| 6,164,284 | A | 12/2000 | Schulman et al. |
| 6,178,349 | B1 | 1/2001 | Kieval |
| 6,181,966 | B1 | 1/2001 | Nigam |
| 6,195,585 | B1 | 2/2001 | Karunasiri et al. |
| 6,224,549 | B1 | 5/2001 | Drongelen |
| 6,240,314 | B1 | 5/2001 | Plicchi et al. |
| 6,240,316 | B1 | 5/2001 | Richmond et al. |
| 6,272,377 | B1 | 8/2001 | Sweeney et al. |
| 6,292,695 | B1 | 9/2001 | Webster, Jr. et al. |
| 6,371,922 | B1 | 4/2002 | Baumann et al. |
| 6,400,982 | B2 | 6/2002 | Sweeney et al. |
| 6,421,557 | B1 | 7/2002 | Meyer |
| 6,449,507 | B1 | 9/2002 | Hill et al. |
| 6,473,644 | B1 | 10/2002 | Terry, Jr. et al. |
| 6,487,450 | B1 | 11/2002 | Chen et al. |
| 6,493,585 | B2 | 12/2002 | Plicchi et al. |
| 6,511,500 | B1 | 1/2003 | Rahme |
| 6,522,926 | B1 | 2/2003 | Kieval et al. |
| 6,532,388 | B1 | 3/2003 | Hill et al. |
| 6,542,774 | B2 | 4/2003 | Hill et al. |
| 6,564,096 | B2 | 5/2003 | Mest |
| 6,583,796 | B2 | 6/2003 | Jamar et al. |
| 6,587,725 | B1 | 7/2003 | Durand et al. |
| 6,611,713 | B2 | 8/2003 | Schauerte |
| 6,622,041 | B2 | 9/2003 | Terry, Jr. et al. |
| 6,628,987 | B1 | 9/2003 | Hill et al. |
| 6,658,287 | B1 | 12/2003 | Litt et al. |
| 6,695,885 | B2 | 2/2004 | Schulman et al. |
| 6,804,561 | B2 | 10/2004 | Stover |
| 6,993,388 | B2 | 1/2006 | Bullinga |
| 7,020,521 | B1 | 3/2006 | Brewer et al. |
| 7,123,961 | B1 | 10/2006 | Kroll et al. |
| 7,123,967 | B2 | 10/2006 | Weinberg |
| 7,225,016 | B1 | 5/2007 | Koh |
| 7,260,431 | B2 | 8/2007 | Libbus et al. |
| 7,277,761 | B2 | 10/2007 | Shelchuk |
| 2002/0026221 | A1 | 2/2002 | Hill et al. |
| 2002/0026222 | A1 | 2/2002 | Schauerte et al. |
| 2002/0042637 | A1 | 4/2002 | Stover |
| 2002/0058877 | A1 | 5/2002 | Baumann et al. |
| 2002/0068875 | A1 | 6/2002 | Schroeppel et al. |
| 2002/0107553 | A1 | 8/2002 | Hill et al. |
| 2002/0107557 | A1 | 8/2002 | Edeii et al. |
| 2002/0120304 | A1 | 8/2002 | Mest |
| 2002/0143369 | A1 | 10/2002 | Hill et al. |
| 2002/0165586 | A1 | 11/2002 | Hill et al. |
| 2003/0003052 | A1 | 1/2003 | Hampton |
| 2003/0004549 | A1 | 1/2003 | Hill et al. |
| 2003/0040774 | A1 | 2/2003 | Terry et al. |
| 2003/0045909 | A1 | 3/2003 | Gross et al. |
| 2003/0055461 | A1 | 3/2003 | Girouard et al. |
| 2003/0060848 | A1 | 3/2003 | Keival et al. |
| 2003/0060857 | A1 | 3/2003 | Perrson et al. |
| 2003/0060858 | A1 | 3/2003 | Kieval et al. |
| 2003/0078623 | A1 | 4/2003 | Weinberg et al. |
| 2003/0078629 | A1 | 4/2003 | Chen |
| 2003/0100924 | A1 | 5/2003 | Foreman et al. |
| 2003/0114905 | A1 | 6/2003 | Kuzma |
| 2003/0149450 | A1 | 8/2003 | Mayberg |
| 2003/0158584 | A1 | 8/2003 | Cates et al. |
| 2003/0195578 | A1 | 10/2003 | Perron et al. |
| 2003/0212440 | A1 | 11/2003 | Boveja |
| 2003/0212445 | A1 | 11/2003 | Weinberg |
| 2004/0131998 | A1 * | 7/2004 | Marom et al. ............... 434/236 |
| 2004/0138517 | A1 * | 7/2004 | Osorio et al. ............... 600/9 |
| 2004/0138579 | A1 | 7/2004 | Deadwyler et al. |
| 2004/0199210 | A1 | 10/2004 | Shelchuk |
| 2004/0210261 | A1 | 10/2004 | King et al. |
| 2004/0215263 | A1 | 10/2004 | Virag et al. |
| 2005/0060001 | A1 | 3/2005 | Singhal et al. |
| 2005/0080348 | A1 | 4/2005 | Stahmann et al. |
| 2005/0085864 | A1 | 4/2005 | Schulman et al. |
| 2005/0096705 | A1 | 5/2005 | Pastore et al. |
| 2005/0143779 | A1 | 6/2005 | Libbus |
| 2005/0143785 | A1 | 6/2005 | Libbus |
| 2005/0149126 | A1 | 7/2005 | Libbus |
| 2005/0149127 | A1 | 7/2005 | Libbus |
| 2005/0149128 | A1 | 7/2005 | Heil, Jr. et al. |
| 2005/0149129 | A1 | 7/2005 | Libbus et al. |
| 2005/0149130 | A1 | 7/2005 | Libbus |
| 2005/0149131 | A1 | 7/2005 | Libbus et al. |
| 2005/0149132 | A1 | 7/2005 | Libbus |
| 2005/0149133 | A1 | 7/2005 | Libbus et al. |
| 2005/0149143 | A1 | 7/2005 | Libbus et al. |
| 2005/0149155 | A1 | 7/2005 | Scheiner et al. |
| 2005/0149156 | A1 | 7/2005 | Libbus et al. |
| 2005/0261741 | A1 | 11/2005 | Libbus et al. |
| 2005/0288718 | A1 | 12/2005 | Sunagawa et al. |
| 2006/0106428 | A1 | 5/2006 | Libbus et al. |
| 2006/0116737 | A1 | 6/2006 | Libbus |
| 2006/0135998 | A1 | 6/2006 | Libbus et al. |
| 2006/0167497 | A1 | 7/2006 | Armstrong et al. |
| 2006/0241697 | A1 | 10/2006 | Libbus et al. |
| 2006/0241725 | A1 | 10/2006 | Libbus |
| 2007/0021799 | A1 | 1/2007 | Kieval et al. |
| 2007/0142864 | A1 | 6/2007 | Libbus et al. |
| 2008/0167694 | A1 | 7/2008 | Bolea et al. |
| 2008/0228238 | A1 | 9/2008 | Libbus |

FOREIGN PATENT DOCUMENTS

| | | |
|---|---|---|
| EP | 0721786 A2 | 7/1996 |
| WO | WO-2006055436 A1 | 5/2005 |
| WO | WO-2006055849 A1 | 5/2006 |
| WO | WO-2008063396 A1 | 5/2008 |

OTHER PUBLICATIONS

Andersen, H., "Long-term follow-up of patients from a randomised trial of atrial versus ventricular pacing for sick-sinus syndrome", *Lancet*, 350(9086), (Oct. 25, 1997), 1210-6.

Benchimol, A., "Cardiac hemodynamics during stimulation of the right atrium, right ventricle, and left ventricle in normal and abnormal hearts", *Circulation*, 33(6), (Jun. 1966),933-44.

Bevan, J. A., et al., "Postganglionic sympathetic delay in vascular smooth muscle", *Journal of Pharmacology & Experimental Therapeutics*, 152(2), (May 1966), 221-30.

Bevan, J. A., et al., "Sympathetic nerve-free vascular muscle", *Journal of Pharmacology& Experimental Therapeutics*, 157(1), (Jul. 1967), 117-24.

Bilgutay, A. M., "A new concept in the treatment of hypertension utilizing an implantable electronic device: "Baropacer"", *Trans Am Soc Artif Intern Organs.*, 10, (1964), 387-95.

Bilgutay, A. M., "Vagal tuning for the control of supraventricular arrhythmias", *Surgical Forum*, 16, (1965), 151-3.

Bilgutay, Aydin M., "Vagal tuning. A new concept in the treatment of supraventricular arrhythmias, angina pectoris, and heart failure", *Journal of Thoracic and Cardiovascular Surgery*, 56(1), (Jul. 1968), 71-82.

Borst, C., "Optimal frequency of carotid sinus nerve stimulation in treatment of angina pectoris", *Cardiovascular Research*, 8(5), (Sep. 1974),674-80.

Braunwald, E., "Carotid sinus nerve stimulation in the treatment of angina pectoris and supraventricular tachycardia", *California Medicine*, 112(3), (Mar. 1970), 41-50.

Braunwald, E., "Relief of angina pectoris by electrical stimulation of the carotid-sinus nerves", *New England Journal of Medicine*, 277(24), (Dec. 14, 1967), 1278-83.

Chapleau, Mark W., "Contrasting effects of static and pulsatile pressure on carotid baroreceptor activity in dogs", *Circulation*, vol. 61, No. 5, (Nov. 1987), 648-658.

Chapleau, M. W., "Neuro-cardiovascular regulation: from molecules to man. Introduction.", *Annals of the New York Academy of Sciences*, 940, (Jun. 2001), xiii-xxii.

Chapleau, Mark W., "Pulsatile activation of baroreceptors causes central facilitation of baroreflex", *American Journal Physiol Heart Circ Physiol*, (Jun. 1989), 256: H1735-1741.

Coleridge, J. C., et al., "Relationship between pulmonary arterial pressure and impulse activity in pulmonary arterial baroreceptor fibres", *Journal of Physiology*, 158, (Sep. 1961), 197-205.

Coleridge, J. C., et al., "The distribution, connexions and histology of baroreceptors in the pulmonary artery, with some observations on the sensory innervation of the ducts arteriosus", *Journal of Physiology*, 156, (May 1961), 591-602.

Cooper, T. B., "Neural effects on sinus rate and atrioventricular conduction produced by electrical stimulation from a transvenous electrode catheter in the canine right pulmonary artery", *Circulation Research*, 46(1), (Jan. 1980), 48-57.

Courtice, G. P., "Effect of frequency and impulse pattern on the non-cholinergic cardiac response to vagal stimulation in the toad, Bufo marinus", *Journal of the Autonomic Nervous System*, 48(3), (Aug. 1994), 267-72.

Dart Jr., C. H., "Carotid sinus nerve stimulation treatment of angina refractory to other surgical procedures", *Annals of Thoracic Surgery*, 11(4), (Apr. 1971), 348-59.

De Landsheere, D., "Effect of spinal cord stimulation on regional myocardial perfusion assessed by positron emission tomography", *American Journal of Cardiology*, 69(14), (May 1, 1992), 1143-9.

Diedrich, A., "Analysis of raw microneurographic recordings based on wavelet de-noising technique and classification algorithm: wavelet analysis in microneurography", *IEEE Transactions on Biomedical Engineering*, 50(1), (Jan. 2003), 41-50.

Dunning, Arend J., "Electrostimulation of the Carotid Sinus Nerve in Angina Pectoris", *University Department of Medicine, Binnengasthuis, Amsterdam; Printed by Royal VanGorcum*, Assen, Netherlands, (1971), 1-92.

Epstein, S. E., "Treatment of angina pectoris by electrical stimulation of the carotid-sinus nerves", *New England Journal of Medicine*, 280(18), (May 1, 1969), 971-8.

Farrehi, C., "Stimulation of the carotid sinus nerve in treatment of angina pectoris", *American Heart Journal*, 80(6) (Dec. 1970), 759-65.

Feliciano, L., "Vagal nerve stimulation releases vasoactive intestinal peptide which significantly increases coronary artery blood flow", *Cardiovascular Research*, 40(1), (Oct. 1998), 45-55.

Fromer, M., "Ultrarapid subthreshold stimulation for termination of atrioventricular node reentrant tachycardia", *Journal of the American College of Cardiology*, 20(4), (Oct. 1992), 879-83.

Grassi, Guido., et al., "Baroreflex and non-baroreflex modulation of vagal cardiac control after myocardial infarction", *Am J Cardiol.*, 84(5), (Sep. 1, 1999), 525-9.

Griffith, Lawrence S., et al., "Electrical Stimulation of the Carotid Sinus Nerve in Normotensive and Renal Hypertensive Dogs", *Circulation*, 28, (Jul.-Dec. 1963), 730.

Henning, R. J., "Effects of autonomic nerve stimulation, asychrony, and load on dP/dtmax and on dP/dtmin", *American Journal of Physiology*, 260(4 Pt 2), (Apr. 1991), H1290-8.

Henning, R. J., "Vagal nerve stimulation increases right ventricular contraction and relaxation and heart rate", *Cardiovascular Research*, 32(5), (Nov. 1996), 846-53.

Henning, R. J., "Vagal stimulation attenuates sympathetic enhancement of left ventricular function", *American Journal of Physiology*, 258(5 Pt 2), (May 1990), H1470-5.

Hood Jr., W. B., et al., "Asynchronous contraction due to late systolic bulging at left ventricular pacing sites", *American Journal of Physiology*, 217(1), (Jul. 1969), 215-21.

Ishise, H., "Time course of sympathovagal imbalance and left ventricular dysfunction in conscious dogs with heart failure", *Journal of Applied Physiology*, 84(4), (Apr. 1998), 1234-41.

Jessurun, G. A., "Coronary blood flow dynamics during transcutaneous electrical nerve stimulation for stable angina pectoris associated with severe narrowing of one major coronary artery", *American Journal of Cardiology*, 82(8), erratum appears in Am J Cardiol Feb 15, 1999;83(4):642, (Oct. 15, 1998), 921-6.

Kandel, Eric R., et al., "Part VII: Arousal, Emotion, and Behavioral Homeostasis", *In: Principles of neural science*, New York : McGraw-Hill, Health Professions Divison, (2000), 966-969.

Karpawich, P. P., et al., "Altered cardiac histology following apical right ventricular pacing in patients with congenital atrioventricular block", *Pacing Clin Electrophysiol.*, 22(9), (Sep. 1999), 1372-7.

Leclercq, C., et al., "Hemodynamic importance of preserving the normal sequence of ventricular activation in permanent cardiac pacing", *Am Heart J.*, 129(6), (Jun. 1995), 1133-41.

Li, Meihua, "Vagal nerve stimulation markedly improves long-term survival after chronic heart failure in rats", *Circulation*, 109(1), Epub Dec. 8, 2003,(Jan. 6, 2004), 1-5.

Libbus, Imad, "Cardiac Rhythm Management Device With Neural Sensor", U.S. Appl. No. 10/992,320, filed Nov. 18. 2004, 65 pgs.

Libbus, I., et al., "Method and Apparatus for Synchronizing Neural Simulation to Cardiac Cycles", U.S. Appl. No. 11/099,141, filed Apr. 5, 2005.

Mannheimer, C., "Epidural spinal electrical stimulation in severe angina pectoris", *British Heart Journal*, 59(1), (Jan. 1988), 56-61.

Mannheimer, C., "Transcutaneous electrical nerve stimulation (TENS) in angina pectoris", *Pain*, 26(3), (Sep. 1986), 291-300.

Mannheimer, C., "Transcutaneous electrical nerve stimulation in severe angina pectoris", *European Heart Journal*, 3(4), (Aug. 1982), 297-302.

Mazgalev, T. N., "Autonomic modification of the atrioventricular node during atrial fibrillation: role in the slowing of ventricular rate", *Circulation*, 99(21), (Jun. 1, 1999), 2806-14.

Millar-Craig, M. W., et al., "Circadian variation of blood-pressure", *Lancet*, 1(8068), (Apr. 15, 1978), 795-7.

Minisi, A J., et al., "Regional left ventricular deafferentation increases baroreflex sensitivity following myocardial infarction", *Cardiovasc Res.*, 58(1), (Apr. 1, 2003), 136-41.

Murphy, D. F., "Intractable angina pectoris: management with dorsal column stimulation", *Medical Journal of Australia*, 146(5), (Mar. 2, 1987), 260.

Neistadt, A., et al., "Effects of electrical stimulation of the carotid sinus nerve in reversal of experimentally induced hypertension", *Surgery*, 61(6), (Jun. 1967),923-31.

Peters, T. K., "Temporal and spatial summation caused by aortic nerve stimulation in rabbits. Effects of stimulation frequencies and amplitudes", *Journal of the Autonomic Nervous System*, 27(3), (Aug. 1989), 193-205.

Peters, T. K., "The principle of electrical carotid sinus nerve stimulation: a nerve pacemaker system for angina pectoris and hypertension therapy", *Annals of Biomedical Engineering*, 8(4-6), (1980), 445-58.

Philbin, D. M., et al., "Inappropriate shocks delivered by an ICD as a result of sensed potentials from a transcutaneous electronic nerve stimulation unit", *Pacing& Clinical Electrophysiology*, 21(10), (Oct. 1998), 2010-1.

Prakash, P., et al., "Asymmetrical distribution of aortic nerve fibers in the pig", *Anat Rec.*, 158(1), (May 1967), 51-7.

Rosenqvist, M., "The effect of ventricular activation sequence on cardiac performance during pacing", *Pacing and Electrophysiology*, 19(9), (1996), 1279-1286.

Rushmer, Robert F., "Chapter 5—Systemic Arterial Pressure", *In: Cardiovascular dynamics*, Philadelphia : Saunders, (1976), 176-216.

Schauerte, P., "Catheter stimulation of cardiac parasympathetic nerves in humans: a novel approach to the cardiac autonomic nervous system", *Circulation*, 104(20), (Nov. 13, 2001), 2430-5.

Schauerte, Patrick N., et al., "Transvenous parasympathetic cardiac nerve stimulation: an approach for stable sinus rate control", *Journal of Cardiovascular Electrophysiology*, 10(11), (Nov. 1999), 1517-24.

Schauerte, Patrick N., et al., "Transvenous Parasympathetic Nerve Stimulation in the Inferior Vena Cava and Atrioventricular Conduction", *Journal of Cardiovascular Electrophysiology*, 11(1), (Jan. 2000), 64-69.

Schauerte, P., "Ventricular rate control during atrial fibrillation by cardiac parasympathetic nerve stimulation: a transvenous approach", *Journal of the American College of Cardiology*, 34(7), (Dec. 1999), 2043-50.

Scherlag, M. A., "Endovascular Neural Stimulation Via a Novel Basket Electrode Catheter: Comparison of Electrode Configurations", *Journal of Interventional Cardiac Electrophysiology*, 4(1), (Apr. 2000), 219-224.

Sigurdsson, Axel, et al., "The role of neurohormonal activation in chronic heart failure and postmyocardial infarction", *American Heart Journal*, 132 (1 Pt 2 Su), (Jul. 1996), 229-234.

Takahashi, N., "Vagal modulation of ventricular tachyarrhythmias induced by left ansae subclaviae stimulation in rabbits", *Japanese Heart Journal*, 39(4), (Jul. 1998), 503-11.

Tse, H. F., et al., "Long-term effect of right ventricular pacing on myocardial perfusion and function", *J Am Coll Cardiol.*, 29(4), (Mar. 15, 1997), 744-9.

Vanoli, Emilio, et al., "Vagal stimulation and prevention of sudden death in conscious dogs with a healed myocardial infarction", *Circulation Research*, 68(5), (May 1991), 1471-81.

Veerman, D. P., et al., "Circadian profile of systemic hemodynamics", *Hypertension*, 26(1), (Jul. 1995); 55-9.

Verity, M. A., et al., "Plurivesicular nerve endings in the pulmonary artery", *Nature*, 211(48), (Jul. 30, 1966), 537-8.

Verity, M., et al., "Pulmonary artery innervation: a morphopharmacologic correlation", *Proceedings of the Western Pharmacology Society*, 8, (1965), 57-9.

Wallick, D. W., "Selective AV nodal vagal stimulation improves hemodynamics during acute atrial fibrillation in dogs", *American Journal of Physiology—Heart& Circulatory Physiology*, 281(4), (Oct. 2001), H1490-7.

Waninger, M. S., "Electrophysiological control of ventricular rate during atrial fibrillation", *Pacing& Clinical Electrophysiology*, 23(8), (Aug. 2000), 1239-44.

Wiggers, C. J., et al., "The muscular reactions of the mammalian ventricles to artificial surface stimuli", *American Journal of Physiology*, (1925), 346-378.

Yanagiya, Y., et al., "Bionic epidural stimulation restores arterial pressure regulation during orthostasis", *J. Appl. Physiol*, 97(3), (Sep. 2004),984-90.

Zhang, Y., "Optimal ventricular rate slowing during atrial fibrillation by feedback AV nodal-selective vagal stimulation", *American Journal of Physiology—Heart& Circulatory Physiology*, 282(3), (Mar. 2002), H1102-10.

Zhou, X., "Prevention of high incidence of neurally mediated ventricular arrhythmias by afferent nerve stimulation in dogs", *Circulation*, 101(7), (Feb. 22, 2000), 819-24.

"U.S. Appl. No. 11/113,773 Non-Final Office Action mailed Jun. 25, 2008", 15 pgs.

"European Application Serial No. 05851890.3, Office Action mailed May 19, 2008", 6 pgs.

"Application Serial No. 05851890.3, Summons to Oral Proceedings mailed Jul. 13, 2009", 6 pgs.

US 7,583,997, 09/2009, Libbus (withdrawn)

\* cited by examiner

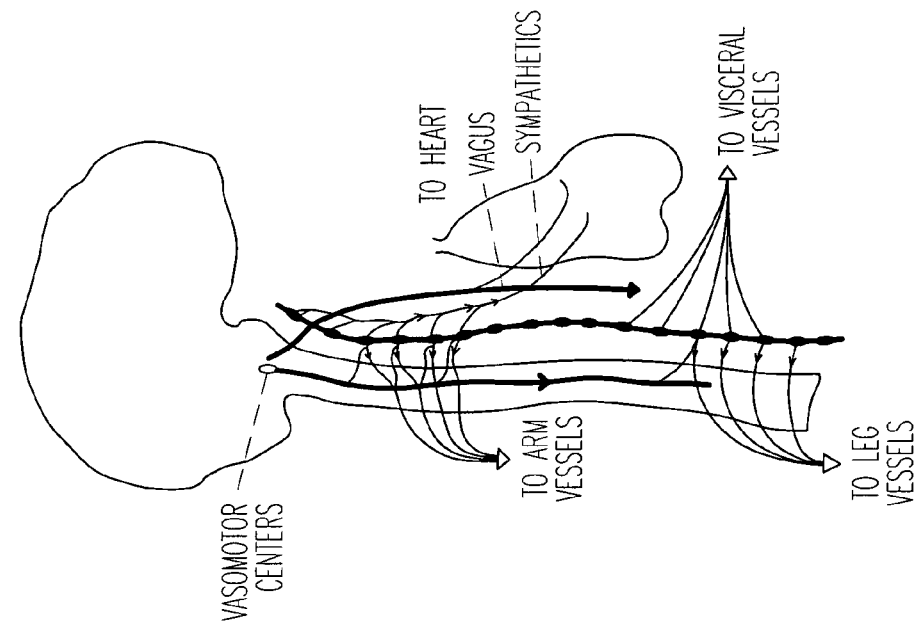
Fig. 1B
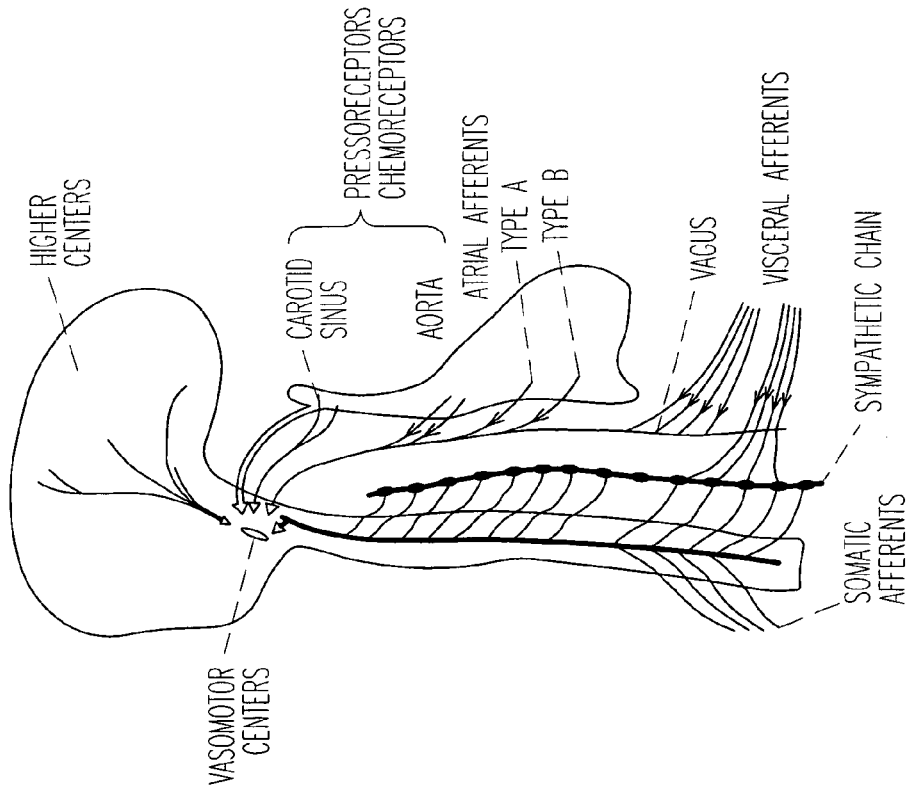
Fig. 1A
Fig. 1

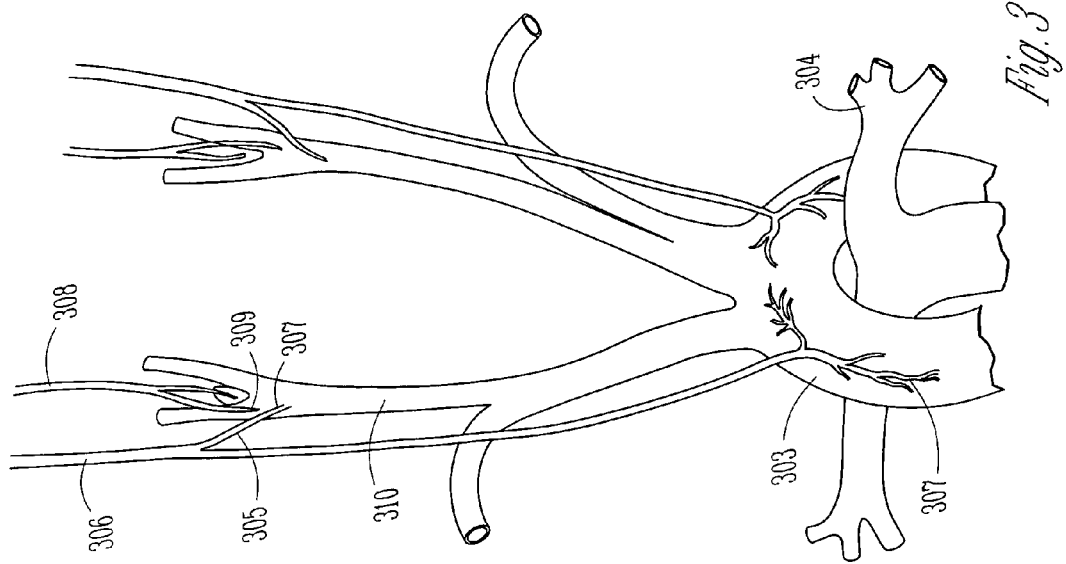
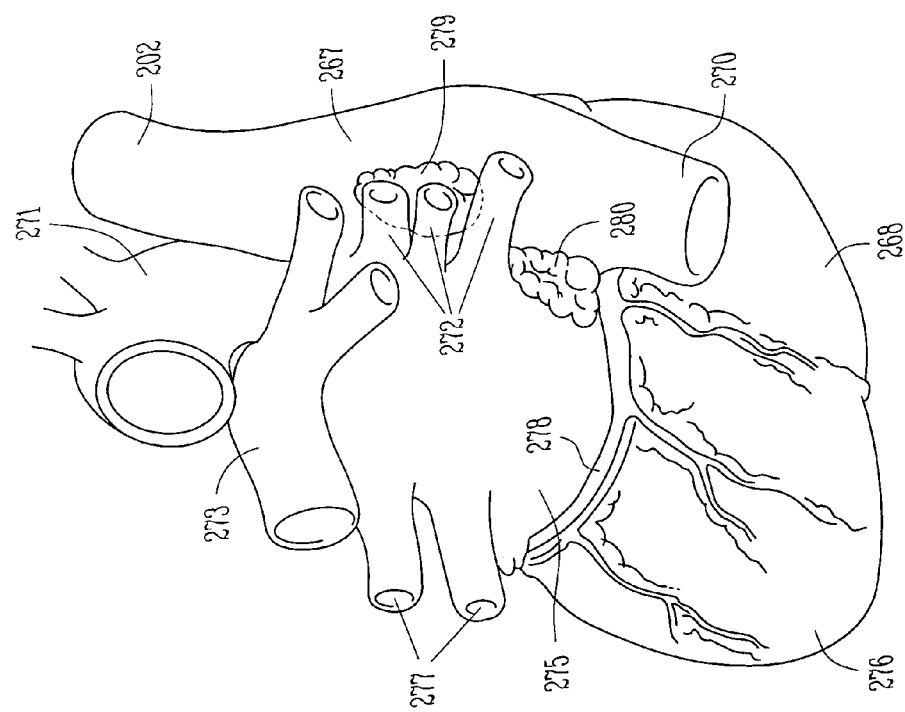

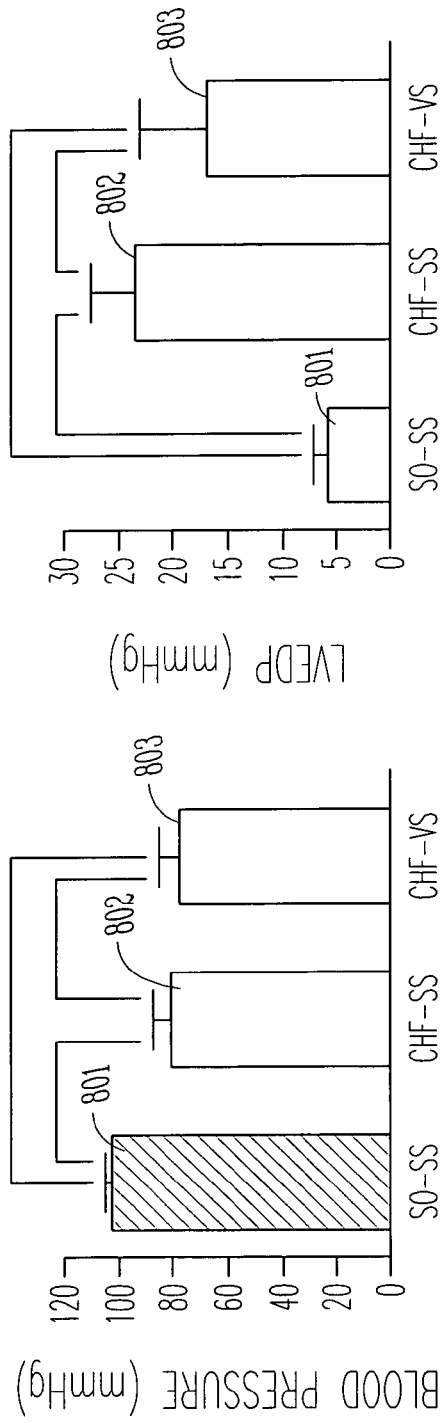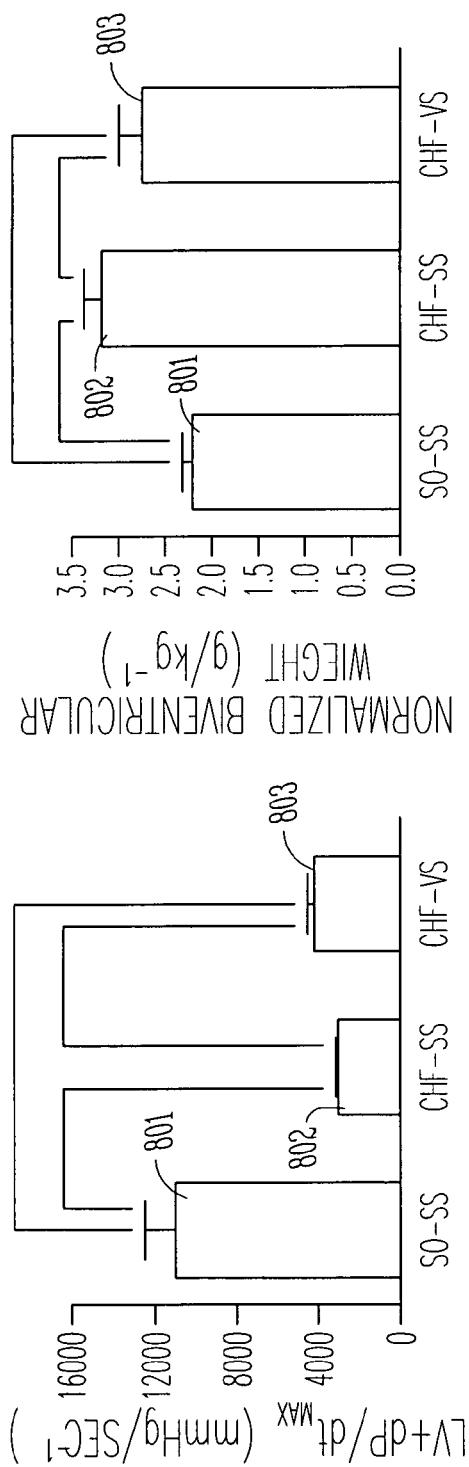
Fig. 8B

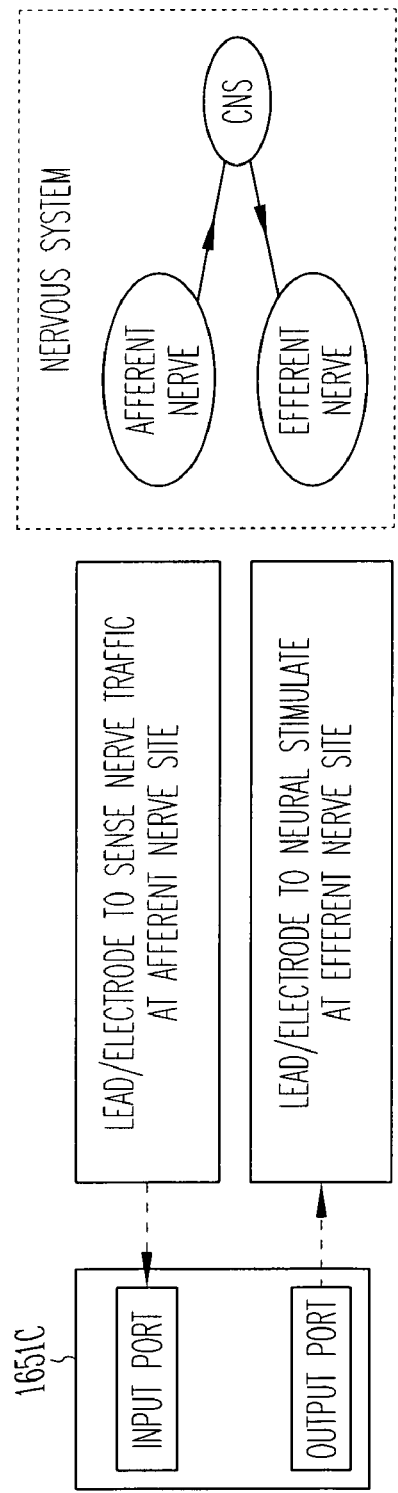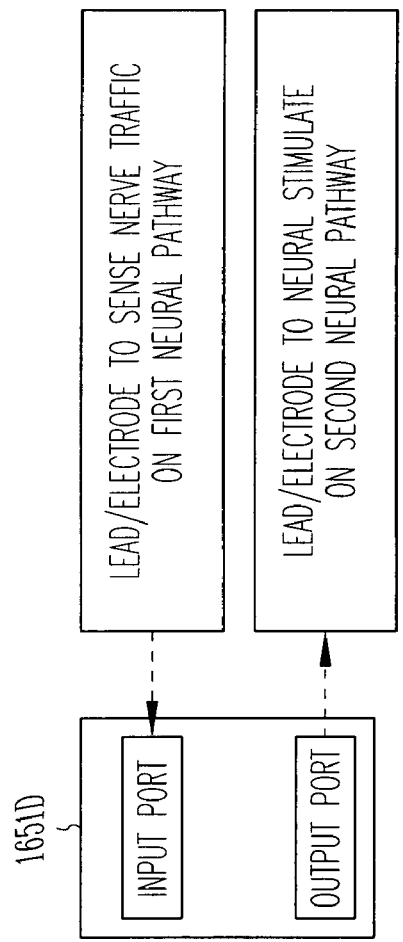

SYSTEM AND METHOD FOR CLOSED-LOOP NEURAL STIMULATION

CROSS REFERENCE TO RELATED APPLICATIONS

The following commonly assigned U.S. patent applications are related, and are herein incorporated by reference in their entirety: "Automatic Baroreflex Modulation Based on Cardiac Activity," Ser. No. 10/746,846, filed on Dec. 24, 2003; and "Cardiac Rhythm Management Device With Neural Sensor," Ser. No. 10/992,320, filed on Nov. 18, 2004.

TECHNICAL FIELD

This application relates generally to neural stimulation systems and, more particularly, to systems, devices and methods for sensing nerve traffic and providing closed-loop neural stimulation based on sensed nerve traffic.

BACKGROUND

Neural stimulators are used to treat a variety of disorders, such as epilepsy, obesity, and breathing disorders. Experimentally, neural stimulation has been shown to have a significant effect on several cardiovascular conditions, and has been proposed to treat hypertension, post myocardial infarction (MI) remodeling and heart failure.

Hypertension is a cause of heart disease and other related cardiac co-morbidities. Hypertension occurs when blood vessels constrict. As a result, the heart works harder to maintain flow at a higher blood pressure, which can contribute to heart failure. A large segment of the general population, as well as a large segment of patients implanted with pacemakers or defibrillators, suffer from hypertension. The long term mortality as well as the quality of life can be improved for this population if blood pressure and hypertension can be reduced. Many patients who suffer from hypertension do not respond to treatment, such as treatments related to lifestyle changes and hypertension drugs.

Direct electrical stimulation has been applied to afferent nerve trunks, including the vagus nerve and carotid sinus. Research has indicated that electrical stimulation of the carotid sinus nerve can result in reduction of experimental hypertension, and that direct electrical stimulation to the pressoreceptive regions of the carotid sinus itself brings about reflex reduction in experimental hypertension. Electrical systems have been proposed to treat hypertension in patients who do not otherwise respond to therapy involving lifestyle changes and hypertension drugs, and possibly to reduce drug dependency for other patients. The stimulation of sympathetic afferents triggers sympathetic activation, parasympathetic inhibition, vasoconstriction, and tachycardia. In contrast, parasympathic activation results in bradycardia, vasodilation and inhibition of vasopressin release.

Neural stimulators that rely on continuous or intermittent open-loop stimulation do not adapt to physiologic changes during therapy.

SUMMARY

Various aspects of the present subject matter relate to a device. In various embodiments, the device comprises a port adapted to connect a lead, a pulse generator connected to the port and adapted to provide a neural stimulation signal to the lead, and a signal processing module connected to the port and adapted to receive and process a nerve traffic signal from the lead into a signal indicative of the nerve traffic. The device includes a controller connected to the pulse generator and the signal processing module. The controller is adapted to implement a stimulation protocol to provide the neural stimulation signal with desired neural stimulation parameters based on the signal indicative of the nerve traffic.

In various embodiments, the device comprises at least a first port adapted to connect a first lead and a second port adapted to connect a second lead, a pulse generator connected to at least the first port and adapted to provide a first neural stimulation signal on the first lead, and a signal processing module connected to at least the second port and adapted to receive and process a nerve traffic signal from the second lead into a first signal indicative of nerve traffic at an electrode of the first lead. The device comprises a controller connected to the pulse generator and the signal processing module. The controller is adapted to implement a stimulation protocol to provide the first neural stimulation signal with desired neural stimulation parameters based on the first signal indicative of the nerve traffic.

Various aspects of the present subject matter relate to a system. In various embodiments, the system comprises means for sensing a nerve traffic signal, means for identifying at least one feature of the nerve traffic signal, and means for applying neural stimulation based on the at least one feature of the nerve traffic signal.

Various aspects of the present subject matter relate to a method. In various embodiments, a nerve traffic signal is sensed, at least one feature of the nerve traffic signal is identified, and neural stimulation based on the at least one feature of the nerve traffic signal is applied.

This Summary is an overview of some of the teachings of the present application and not intended to be an exclusive or exhaustive treatment of the present subject matter. Further details about the present subject matter are found in the detailed description and appended claims. Other aspects will be apparent to persons skilled in the art upon reading and understanding the following detailed description and viewing the drawings that form a part thereof, each of which are not to be taken in a limiting sense. The scope of the present invention is defined by the appended claims and their equivalents.

BRIEF DESCRIPTION OF THE DRAWINGS

FIGS. 1A and 1B illustrate neural mechanisms for peripheral vascular control.

FIGS. 2A-2C illustrate a heart.

FIG. 3 illustrates baroreceptors and afferent nerves in the area of the carotid sinuses and aortic arch.

FIGS. 8A-8C illustrate a known response of vagal nerve stimulation for rats with chronic heart failure (CHF), indicating that vagal nerve stimulation prevented pumping failure and cardiac remodeling and thus improved the long-term survival of CHF rats.

FIGS. 16A-16D illustrate various closed-loop control systems implemented by various neural stimulation device embodiments.

DETAILED DESCRIPTION

Figure 2B:
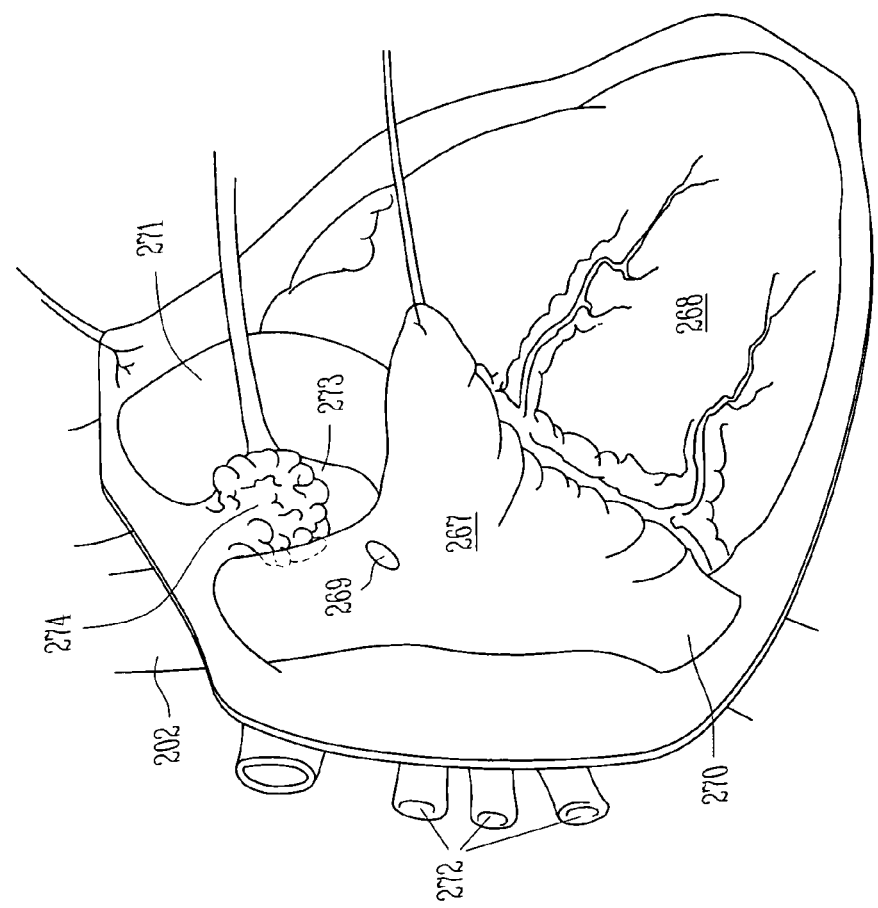

The following detailed description of the present subject matter refers to the accompanying drawings which show, by way of illustration, specific aspects and embodiments in which the present subject matter may be practiced. These embodiments are described in sufficient detail to enable those skilled in the art to practice the present subject matter. Other embodiments may be utilized and structural, logical, and electrical changes may be made without departing from the scope of the present subject matter. References to "an", "one", or "various" embodiments in this disclosure are not necessarily to the same embodiment, and such references contemplate more than one embodiment. The following detailed description is, therefore, not to be taken in a limiting sense, and the scope is defined only by the appended claims, along with the full scope of legal equivalents to which such claims are entitled.

A device is provided with at least one lead for use to perform neural sensing and neural stimulation functions. The device is able to amplify, filter, record and analyze the target nerve activity, and use the resulting information to accurately and appropriately deliver the neural stimulation. Sympathetic nerve activity (SNA) has a low signal amplitude (1-10 µV), and relatively high noise amplitude. Various embodiments provide amplification to provide a gain within a range of approximately 1,000 to approximately 99,000, for example, and bandpass filtering to pass frequencies within a range of approximately 30 Hz to approximately 3,000 Hz, to process neural traffic associated with SNA. Various embodiments use various subsets of these gain and frequency ranges.

Systems and methods are provided for monitoring nerve traffic for use to deliver appropriate neural stimulation. Monitored nerve traffic is used to accurately provide autonomic modulation for accurate and appropriate delivery of neural stimulation. Thus, the present subject mater provides a closed-loop neural stimulation system that allows the neural stimulation device to monitor nerve traffic and continuously provide appropriate therapy. A neural sensing lead is used to record nerve traffic from the peripheral nervous system (such as baroreceptors, afferent nerves and/or efferent nerves) to guide neural stimulation therapy, to record physiologic parameters such as pressure for diagnostic purposes, and/or to guide CRM therapy. Applications include a wide range of cardiovascular and non-cardiovascular diseases, such as hypertension, epilepsy, obesity, breathing disorders, and the like.

A brief description of hypertension and baroreflex is provided below, followed by various systems to provide neural stimulation for hypertension or other therapies.

Hypertension And Baroreflex Physiology

A brief discussion of hypertension and the physiology related to baroreceptors is provided to assist the reader with understanding this disclosure. This brief discussion introduces hypertension, the autonomic nervous system, and baroreflex.

Hypertension is a cause of heart disease and other related cardiac co-morbidities. Hypertension generally relates to high blood pressure, such as a transitory or sustained elevation of systemic arterial blood pressure to a level that is likely to induce cardiovascular damage or other adverse consequences. Hypertension has been arbitrarily defined as a systolic blood pressure above 140 mm Hg or a diastolic blood pressure above 90 mm Hg. Hypertension occurs when blood vessels constrict. As a result, the heart works harder to maintain flow at a higher blood pressure. Consequences of uncontrolled hypertension include, but are not limited to, retinal vascular disease and stroke, left ventricular hypertrophy and failure, myocardial infarction, dissecting aneurysm, and renovascular disease.

The autonomic nervous system (ANS) regulates "involuntary" organs, while the contraction of voluntary (skeletal) muscles is controlled by somatic motor nerves. Examples of involuntary organs include respiratory and digestive organs, and also include blood vessels and the heart. Often, the ANS functions in an involuntary, reflexive manner to regulate glands, to regulate muscles in the skin, eye, stomach, intestines and bladder, and to regulate cardiac muscle and the muscle around blood vessels, for example.

The ANS includes, but is not limited to, the sympathetic nervous system and the parasympathetic nervous system. The sympathetic nervous system is affiliated with stress and the "fight or flight response" to emergencies. Among other effects, the "fight or flight response" increases blood pressure and heart rate to increase skeletal muscle blood flow, and decreases digestion to provide the energy for "fighting or fleeing." The parasympathetic nervous system is affiliated with relaxation and the "rest and digest response" which, among other effects, decreases blood pressure and heart rate, and increases digestion to conserve energy. The ANS maintains normal internal function and works with the somatic nervous system.

Various embodiments of the present subject matter provide neural stimulation to affect the heart rate, blood pressure, vasodilation and vasoconstriction. The heart rate and force is increased when the sympathetic nervous system is stimulated, and is decreased when the sympathetic nervous system is inhibited and the parasympathetic nervous system is stimulated. FIGS. 1A and 1B illustrate neural mechanisms for peripheral vascular control. FIG. 1A generally illustrates afferent nerves to vasomotor centers. An afferent nerve conveys impulses toward a nerve center. FIG. 1B generally illustrates efferent nerves from vasomotor centers. An efferent nerve conveys impulses away from a nerve center.

Stimulating the sympathetic and parasympathetic nervous systems can have effects other than heart rate and blood pressure. For example, stimulating the sympathetic nervous system dilates the pupil, reduces saliva and mucus production, relaxes the bronchial muscle, reduces the successive waves of involuntary contraction (peristalsis) of the stomach and the motility of the stomach, increases the conversion of glycogen to glucose by the liver, decreases urine secretion by the kidneys, and relaxes the wall and closes the sphincter of the bladder. Stimulating the parasympathetic nervous system and/or inhibiting the sympathetic nervous system constricts the pupil, increases saliva and mucus production, contracts the bronchial muscle, increases secretions and motility in the stomach and large intestine, and increases digestion in the small intention, increases urine secretion, and contracts the wall and relaxes the sphincter of the bladder. The functions associated with the sympathetic and parasympathetic nervous systems are many and can be complexly integrated with each other. Thus, an indiscriminate stimulation of the sympathetic and/or parasympathetic nervous systems to achieve a desired response, such as vasodilation, in one physiological system may also result in an undesired response in other physiological systems.

A pressoreceptive region or field is capable of sensing changes in pressure, such as changes in blood pressure. Pressoreceptor regions are referred to herein as baroreceptors, which generally include any sensors of pressure changes. For example, baroreceptors include afferent nerves and further include sensory nerve endings that provide baroreceptor fields that are sensitive to the stretching of the wall that results from increased blood pressure from within, and function as the receptor of a central reflex mechanism that tends to reduce the pressure. Baroreflex functions as a negative feedback system, and relates to a reflex mechanism triggered by stimulation of a baroreceptor. Increased pressure stretches blood vessels, which in turn activates baroreceptors in the vessel walls. Activation of baroreceptors naturally occurs through internal pressure and stretching of the arterial wall, which excites the parasympathetic nervous system causing baroreflex inhibition of sympathetic nerve activity (SNA) and a reduction in systemic arterial pressure. An increase in baroreceptor activity induces a reduction of SNA, which reduces blood pressure by decreasing peripheral vascular resistance. Centrally mediated reflex pathways modulate cardiac rate, contractility and excitability. Baroreceptors and chemoreceptors in the heart, great vessels, and lungs, transmit neural signals reflective of cardiac activity through vagal and afferent fibers to the central nervous system. Thus, physiological parameters, such as systemic arterial pressure, can be determined based on nerve traffic. Such pressure information, for example, provides useful feedback information to guide CRM therapy such as CRT.

Baroreflex is a reflex triggered by stimulation of a baroreceptor. A baroreceptor includes any sensor of pressure changes, such as sensory nerve endings in the wall of the auricles of the heart, vena cava, aortic arch and carotid sinus, that is sensitive to stretching of the wall resulting from increased pressure from within, and that functions as the receptor of the central reflex mechanism that tends to reduce that pressure. Afferent nerves can also be electrically stimulated to induce a baroreflex, which inhibits the sympathetic nerve activity and stimulates parasympathetic nerve activity. Afferent nerve trunks, such as the vagus, aortic and carotid nerves, leading from the sensory nerve endings also form part of a baroreflex pathway. Stimulating a baroreflex pathway and/or baroreceptors inhibits sympathetic nerve activity, stimulates the parasympathetic nervous system and reduces systemic arterial pressure by decreasing peripheral vascular resistance and cardiac contractility. Baroreceptors are naturally stimulated by internal pressure and the stretching of vessel wall (e.g. arterial wall).

Embodiments of the present subject matter provide neural stimulation and receive sensed nerve traffic information to provide a closed-loop neural stimulator system with neural activity feedback. Some aspects of the present subject matter locally sense and/or stimulate specific nerve endings in vessel walls rather than or in addition to afferent and/or efferent nerve trunks. For example, some embodiments sense and/or stimulate baroreceptor sites or fields in the pulmonary artery. Some embodiments of the present subject matter involve sensing and/or stimulating baroreceptor sites or nerve endings in the aorta, the chambers of the heart, some embodiments of the present subject matter involve sensing and/or stimulating efferent pathways such as the fat pads of the heart, and some embodiments of the present subject matter involve sensing and/or stimulating an afferent nerve trunk, such as the vagus, carotid and aortic nerves. Various embodiments involve combinations of sensing and/or stimulating nerve endings, sensing efferent nerve pathways and sensing afferent nerve pathways. Some embodiments sense and/or stimulate nerve trunks using a cuff electrode, and some embodiments sense and/or stimulate nerve trunks using an intravascular lead positioned in a blood vessel proximate to the nerve. Examples of afferent nerve trunks include the vagus, aortic and carotid nerves. Examples of efferent nerve trunks include the cardiac branches off the vagus nerve. Stimulation of efferent nerves such as these cardiac branches or the nerves in cardiac fat pads conveys nervous impulses to an effector, and thus do not use the baroreflex negative feedback of the central nervous system, which responds to nerve activity on afferent nerves with nerve activity on efferent nerves. Some embodiments sense and/or stimulate neural traffic at any of the above-identified neural sites.

Figure 2A:
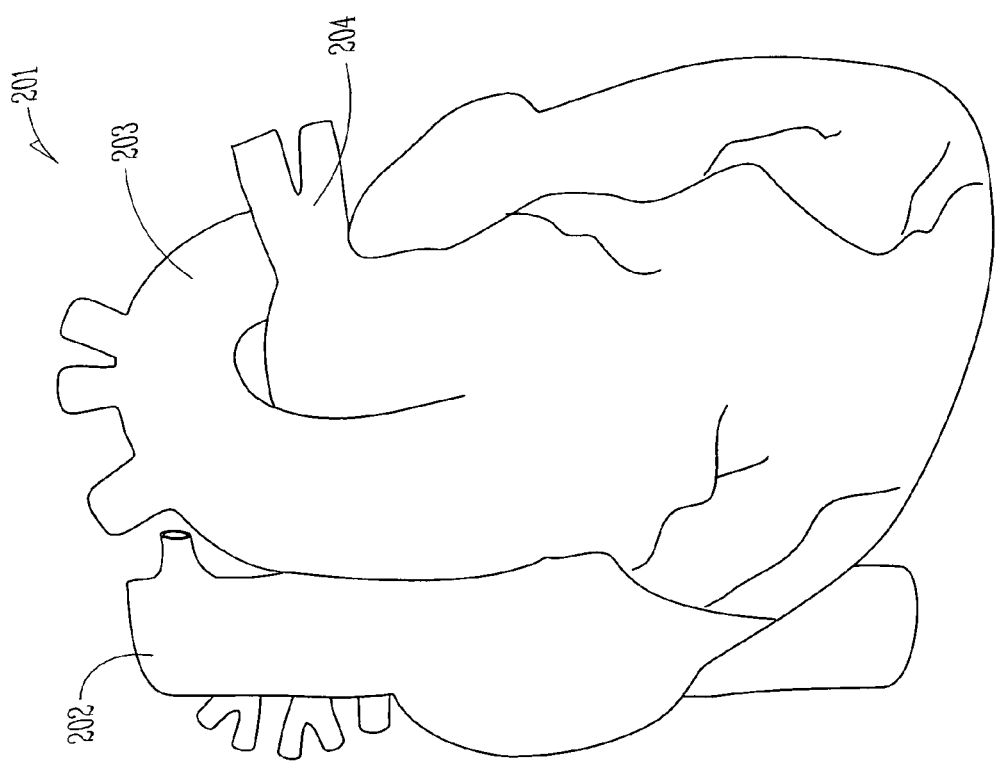

FIGS. 2A-2C illustrate a heart. As illustrated in FIG. 2A, the heart 201 includes a superior vena cava 202, an aortic arch 203, and a pulmonary artery 204, and is useful to provide a contextual relationship with the illustrations in FIGS. 3-5. As is discussed in more detail below, the pulmonary artery 204 includes baroreceptors. A lead is capable of being intravascularly inserted through a peripheral vein and through the tricuspid valve into the right ventricle of the heart (not expressly shown in the figure) similar to a cardiac pacemaker lead, and continue from the right ventricle through the pulmonary valve into the pulmonary artery. A portion of the pulmonary artery and aorta are proximate to each other. Various embodiments stimulate baroreceptors and/or sense neural activity by the baroreceptor in the aorta using a lead intravascularly positioned in the pulmonary artery. Thus, according to various aspects of the present subject matter, the baroreflex is stimulated and/or nerve activity is sensed in or around the pulmonary artery by at least one electrode intravascularly inserted into the pulmonary artery. In various embodiments, a wireless stimulating device, with or without pressure sensing capability, may be positioned via catheter into the pulmonary artery. Control of stimulation and/or energy for stimulation may be supplied by another implantable or external device via ultrasonic, electromagnetic or a combination thereof. Aspects of the present subject matter provide a relatively noninvasive surgical technique to implant a neural traffic sensor, with or without a baroreceptor stimulator, intravascularly into the pulmonary artery.

FIGS. 2B-2C illustrate the right side and left side of the heart, respectively, and further illustrate cardiac fat pads. FIG. 2B illustrates the right atrium 267, right ventricle 268, sinoatrial node 269, superior vena cava 202, inferior vena cava 270, aorta 271, right pulmonary veins 272, and right pulmonary artery 273. FIG. 2B also illustrates a cardiac fat pad 274 between the superior vena cava and aorta. Autonomic ganglia in the cardiac fat pad 274 are stimulated and/or nerve traffic is sensed in some embodiments using an electrode screwed or otherwise inserted into the fat pad, and are stimulated and/or nerve traffic is sensed in some embodiments using an intravenously-fed lead proximately positioned to the fat pad in a vessel such as the right pulmonary artery or superior vena cava, for example. FIG. 2C illustrates the left atrium 275, left ventricle 276, right atrium 267, right ventricle 268, superior vena cava 202, inferior vena cava 270, aorta 271, right pulmonary veins 272, left pulmonary vein 277, right pulmonary artery 273, and coronary sinus 278. FIG. 2C also illustrates a cardiac fat pad 279 located proximate to the right cardiac veins and a cardiac fat pad 280 located proximate to the inferior vena cava and left atrium. Autonomic ganglia in the fat pad 279 are stimulated and/or nerve traffic is sensed in some embodiments using an electrode screwed or otherwise inserted into the fat pad 279, and are stimulated and/or nerve traffic is sensed in some embodiments using an intravenously-fed lead proximately positioned to the fat pad in a vessel such as the right pulmonary artery 273 or right pulmonary vein 272, for example. Autonomic ganglia in the cardiac fat pad 280 are stimulated and/or nerve traffic is sensed in some embodiments using an electrode screwed or otherwise inserted into the fat pad, and are stimulated and/or nerve traffic is sensed in some embodiments using an intravenously-fed lead proximately positioned to the fat pad in a vessel such as the inferior vena cava 270 or coronary sinus or a lead in the left atrium 275, for example.

FIG. 3 illustrates baroreceptors in the area of the carotid sinus 305, aortic arch 303 and pulmonary artery 304. The aortic arch 303 and pulmonary artery 304 were previously illustrated with respect to the heart in FIG. 2A. As illustrated in FIG. 3, the vagus nerve 306 extends and provides sensory nerve endings 307 that function as baroreceptors in the aortic arch 303, in the carotid sinus 305 and in the common carotid artery 310. The glossopharyngeal nerve 308 provides nerve endings 309 that function as baroreceptors in the carotid sinus 305. These nerve endings 307 and 309, for example, are sensitive to stretching of the wall resulting from increased pressure from within. Activation of these nerve endings reduce pressure. Although not illustrated in the figures, the fat pads and the atrial and ventricular chambers of the heart also include baroreceptors. Cuffs have been placed around afferent nerve trunks, such as the vagal nerve, leading from baroreceptors to vasomotor centers to stimulate the baroreflex. According to various embodiments of the present subject matter, afferent nerve trunks can be stimulated using a cuff or intravascularly-fed lead positioned in a blood vessel proximate to the afferent nerves.

Figure 5:
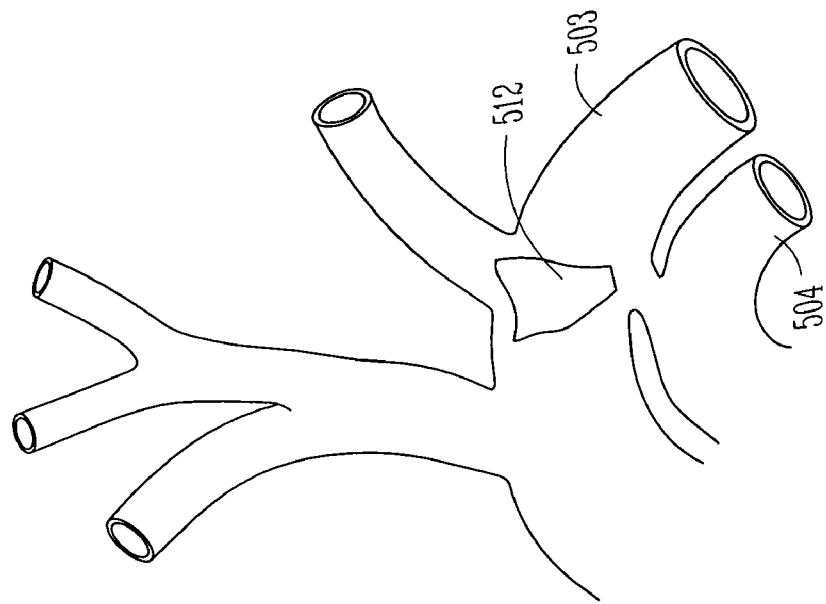
FIG. 5 illustrates baroreceptor fields in the aortic arch, the ligamentum arteriosum and the trunk of the pulmonary artery.
Figure 4:
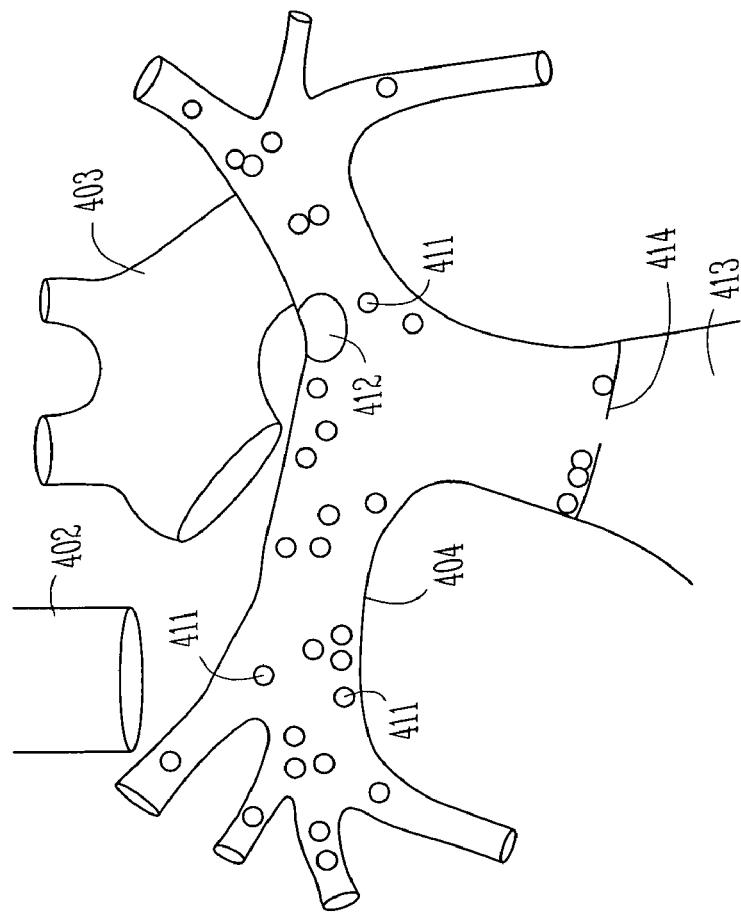
FIG. 4 illustrates baroreceptors in and around the pulmonary artery.

FIG. 4 illustrates baroreceptors in and around a pulmonary artery 404. The superior vena cava 402 and the aortic arch 403 are also illustrated. As illustrated, the pulmonary artery 404 includes a number of baroreceptors 411, as generally indicated by the dark area. Furthermore, a cluster of closely spaced baroreceptors is situated near the attachment of the ligamentum arteriosum 412. FIG. 4 also illustrates the right ventricle 413 of the heart, and the pulmonary valve 414 separating the right ventricle 413 from the pulmonary artery 404. According to various embodiments of the present subject matter, a lead is inserted through a peripheral vein and threaded through the tricuspid valve into the right ventricle, and from the right ventricle 413 through the pulmonary valve 414 and into the pulmonary artery 404 to stimulate baroreceptors in and/or around the pulmonary artery. In various embodiments, for example, the lead is positioned to stimulate the cluster of baroreceptors near the ligamentum arteriosum 412. FIG. 5 illustrates baroreceptor fields 512 in the aortic arch 503, near the ligamentum arteriosum and the trunk of the pulmonary artery 504. Some embodiments position the lead in the pulmonary artery to stimulate baroreceptor sites in the aorta and/or fat pads, such as are illustrated in FIGS. 2B-2C.

Figure 6:
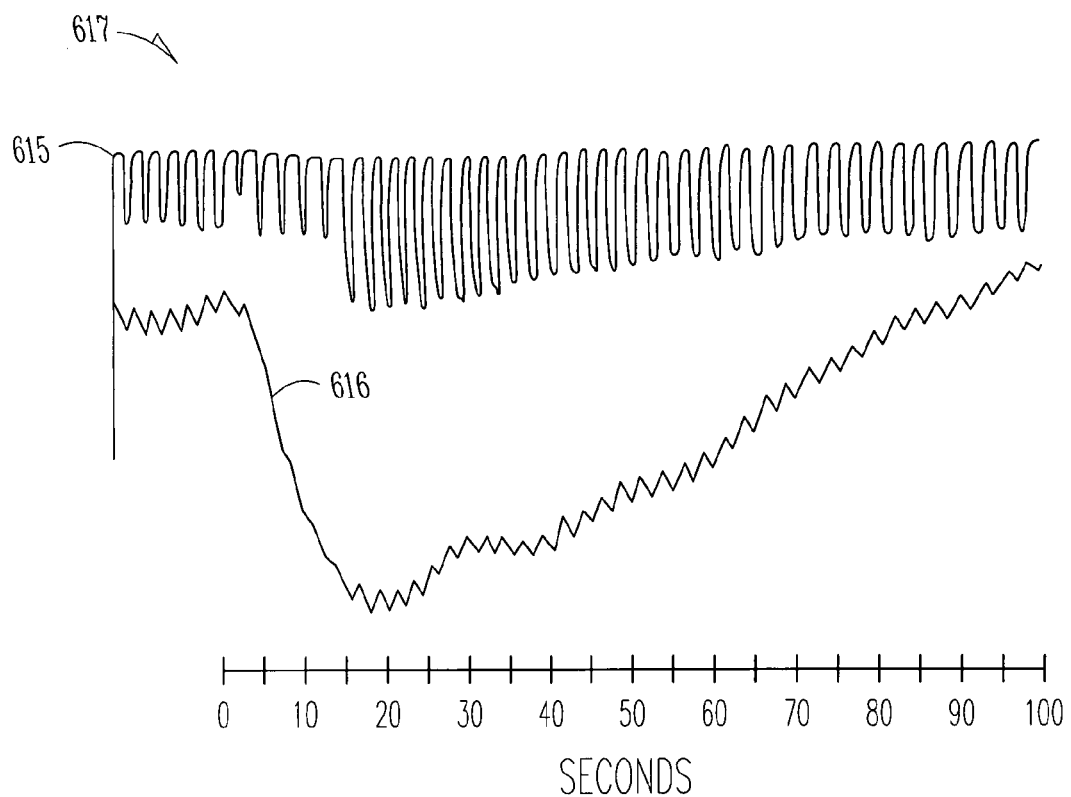
FIG. 6 illustrates a known relationship between respiration and blood pressure when the baroreflex is stimulated.

FIG. 6 illustrates a known relationship between respiration 615 and blood pressure 616 when the left aortic nerve is stimulated. When the nerve is stimulated at 617, the blood pressure 616 drops, and the respiration 615 becomes faster and deeper, as illustrated by the higher frequency and amplitude of the respiration waveform. The respiration and blood pressure appear to return to the pre-stimulated state in approximately one to two minutes after the stimulation is removed. This relationship between respiration and blood pressure allows respiration to be used as a surrogate parameter for blood pressure under some conditions.

Figure 7:
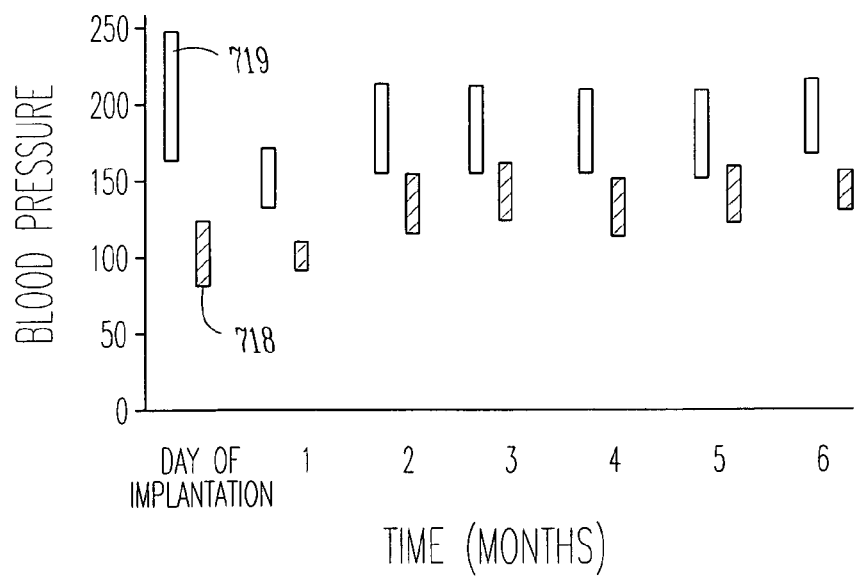
FIG. 7 illustrates a blood pressure response to carotid nerve stimulation in a hypertensive dog during 6 months of intermittent carotid nerve stimulation.

FIG. 7 illustrates a known blood pressure response to carotid nerve stimulation in a hypertensive dog during 6 months of intermittent carotid nerve stimulation. The carotid nerve stimulation involved turning on a carotid nerve stimulator once a month for up to six hours, and measuring the blood pressure response to monitor the stability of the acute response over long time periods. The figure illustrates that the blood pressure of a stimulated dog 718 is significantly less than the blood pressure of a control dog 719 that also has high blood pressure. Thus, such stimulation is capable of triggering the baroreflex to reduce high blood pressure.

Figure 8A:
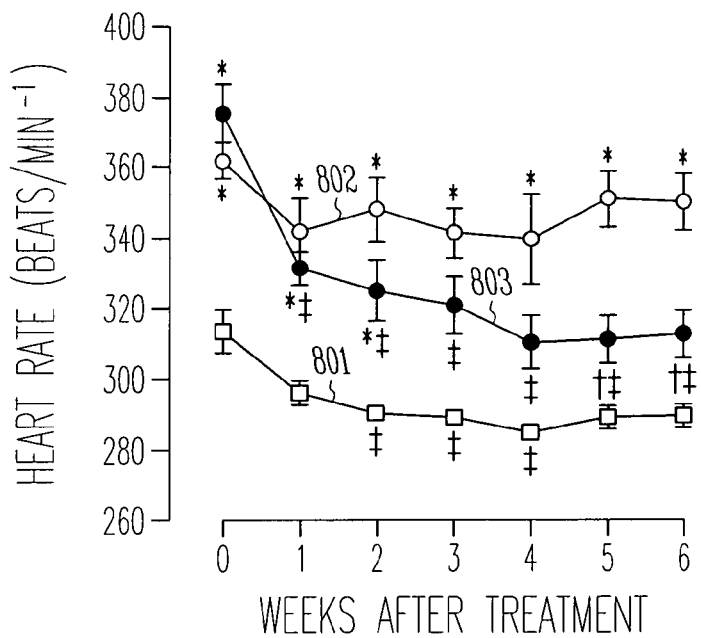
Figure 8C:
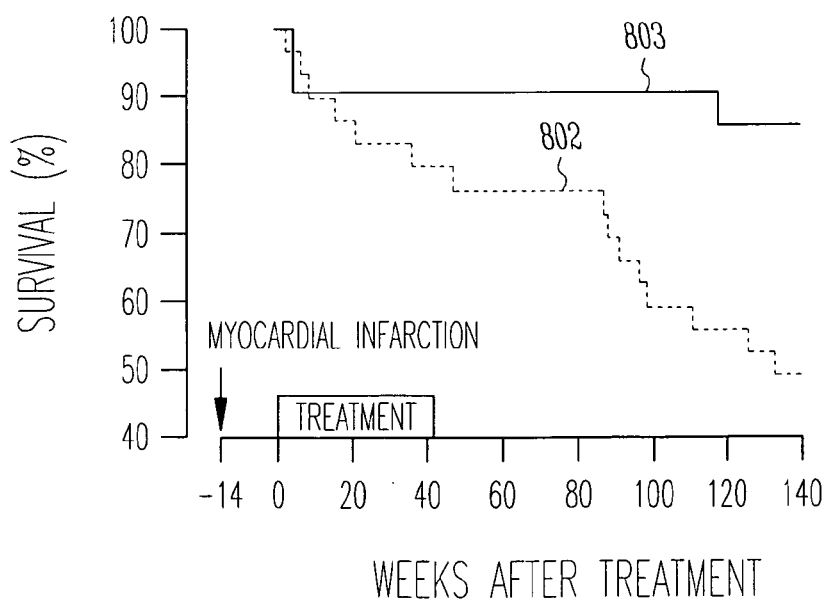

FIGS. 8A-8C illustrate a known response of vagal nerve stimulation for rats with chronic heart failure (CHF), indicating that vagal nerve stimulation prevented pumping failure and cardiac remodeling and thus improved the long-term survival of CHF rats in one study. Previous studies indicated that diminished cardiac vagal activity and increased heart rate predict a high mortality rate of CHF. Ligation of the left coronary artery of the rats induced CHF. Vagal stimulation (rectangular pulses of 0.2 ms duration at 20 Hz for 10 seconds every minute) was performed on some of the CHF rats. Other CHF rats were sham stimulated. Other rats were operated on without inducing CHF. FIGS. 8A-8C include graphs labeled with the numbers 801, 802 and 803, where 801 represents a control group of rats that were operated on without inducing CHF and that are not treated with vagal stimulation, where 802 represents a control group of CHF rats that were sham stimulated, and where 803 represents CHF rats treated with vagal stimulation. FIG. 8A illustrates average heart rates for rats without CHF 801, CHF rats with sham stimulation 802, and CHF rats with vagal stimulation 803. The rats with CHF 802 and 803 had a higher heart rate than the rats without CHF 801. CHF rats undergoing vagal stimulation 803 had significantly decreased heart rates in comparison to CHF rats with sham stimulation 802. FIG. 8B illustrates the effects of vagal nerve stimulation on mean blood pressure, left ventricular end-diastolic pressure (LVEDP), maximum rate of pressure change (dp/dt) of left ventricular pressure (LV+dP/dt$_{max}$), and normalized biventricular weight. FIG. 8B illustrates that the vagal stimulation improved pumping efficiency as evidenced by the lower LVEDP and higher LV+dP/dt$_{max}$ for vagal-stimulated rats 803 compared to sham-stimulated rats 802, and further illustrates that the vagal stimulation decreased the normalized biventricular weight for vagal-stimulated rats 803 compared to sham-stimulated rats 802. FIG. 8C illustrates that vagal nerve stimulation suppressed the mortality rate of CHF rats, as evidenced by the higher survival rate of the vagal-stimulated CHF rats 803 in comparison to the sham-stimulated CHF rats 802.

Systems To Provide Neural Stimulation

Examples of neural stimulators include anti-hypertension (AHT) devices or AHT components that are used to treat hypertension. Various embodiments of the present subject matter include stand-alone implantable neural stimulator systems, and include implantable devices that have integrated NS and cardiac rhythm management (CRM) components, and include systems with at least one implantable NS device and an implantable CRM device capable of communicating with each other either wirelessly or through a wire lead connecting the implantable devices. Although implantable systems are illustrated and discussed, various aspects and embodiments of the present subject matter can be implemented in external devices.

Figure 9A:
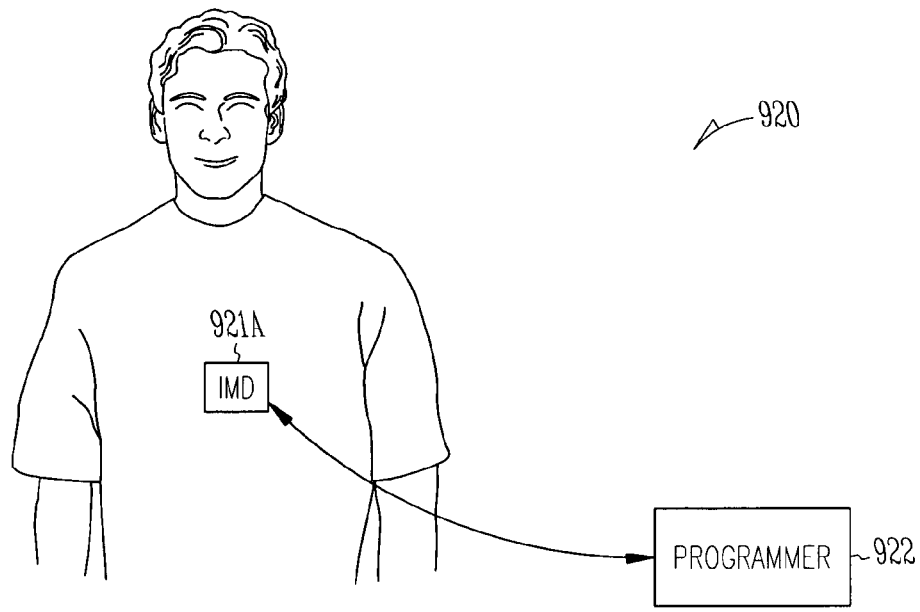
FIG. 9A illustrates a system including an implantable medical device (IMD) and a programmer, according to various embodiments of the present subject matter.

FIG. 9A illustrates a system 920 including an implantable medical device (IMD) 921A and a programmer 922, according to various embodiments of the present subject matter. Various embodiments of the IMD 921A include neural stimulator functions only, various embodiments include CRM functions only, and various embodiments include a combination of NS and CRM functions. Examples of cardiac stimulators include implantable cardiac rhythm management (CRM) devices such as pacemakers, implantable cardiac defibrillators (ICDs), and implantable devices capable of performing pacing and defibrillating functions. Implantable CRM devices provide electrical stimulation to selected chambers of the heart in order to treat disorders of cardiac rhythm. An implantable pacemaker, for example, is a CRM device that paces the heart with timed pacing pulses. The pacing pulses can be timed from other pacing pulses or sensed electrical activity. If functioning properly, the pacemaker makes up for the heart's inability to pace itself at an appropriate rhythm in order to meet metabolic demand by enforcing a minimum heart rate. Some CRM devices synchronize pacing pulses delivered to different areas of the heart in order to coordinate the contractions. Coordinated contractions allow the heart to pump efficiently while providing sufficient cardiac output. Some embodiments of the neural stimulator provide AHT neural stimulation functions to treat hypertension.

The programmer 922 and the IMD 921A are capable of wirelessly communicating data and instructions. In various embodiments, for example, the programmer 922 and IMD 921A use telemetry coils to wirelessly communicate data and instructions. Thus, the programmer can be used to adjust the programmed therapy provided by the IMD 921A, and the IMD can report device data (such as battery and lead resistance) and therapy data (such as sense and stimulation data) to the programmer using radio telemetry, for example. According to various embodiments, the IMD 921A stimulates baroreceptors to provide NS therapy such as AHT therapy. Various embodiments of the IMD 921A stimulate baroreceptors in the pulmonary artery using a lead fed through the right ventricle similar to a cardiac pacemaker lead, and further fed into the pulmonary artery. Other embodiments stimulate other baroreceptor sites or baroreflex pathways or combinations thereof, such as illustrated and described with respect to FIGS. 2A-2C, 3 and 4. According to various embodiments, the IMD 921A includes a sensor to sense ANS activity. Such a sensor can be used to perform feedback in a closed-loop control system. For example, various embodiments sense surrogate parameters, such as respiration and blood pressure, indicative of ANS activity. According to various embodiments, the IMD further includes cardiac stimulation capabilities, such as pacing, cardiac resynchronization therapy (CRT) and defibrillating capabilities in addition to the capabilities to stimulate baroreceptors and/or sense ANS activity. In some embodiments, the illustrated IMD includes two or more devices capable of communicating with each other via wireless technology; and in some embodiments, the illustrated IMD includes two or more devices capable of communicating with each other via a cable or wire, such as an intravenously fed lead.

Figure 9B:
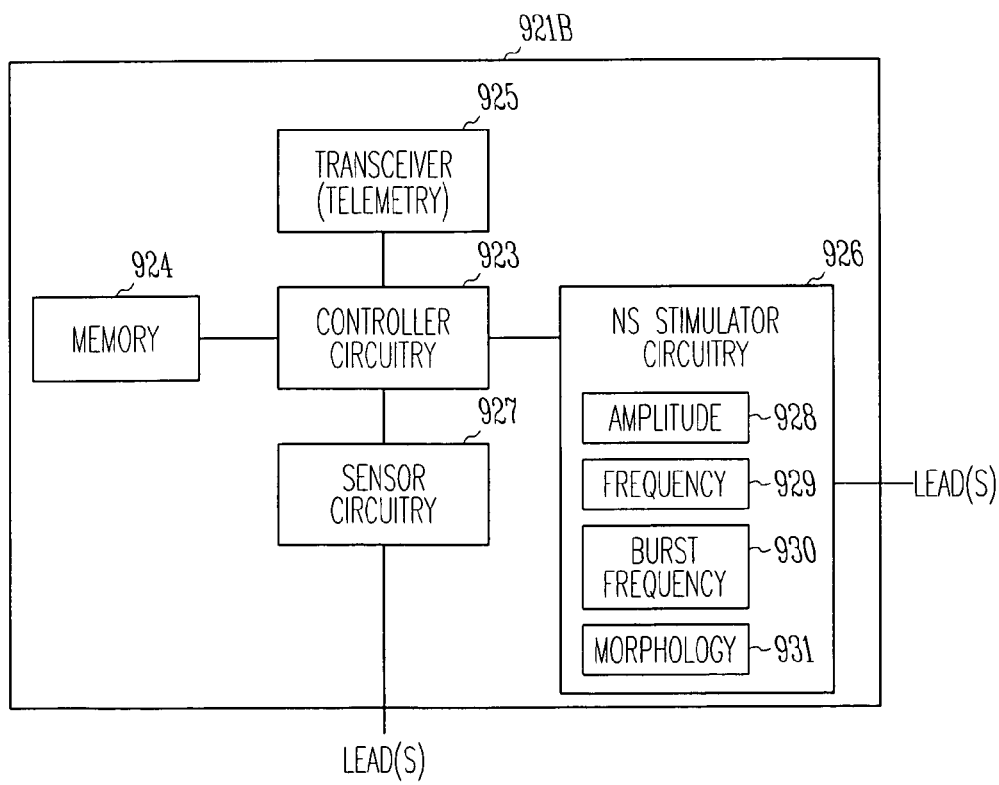
FIG. 9B illustrates an implantable medical device (IMD) such as the IMD shown in the system of FIG. 9A, according to various embodiments of the present subject matter.

FIG. 9B illustrates an implantable medical device (IMD) 921B such as the IMD 921A shown in the system 920 of FIG. 9A, according to various embodiments of the present subject matter. The illustrated IMD 921B performs NS functions. Some embodiments of the illustrated IMD 921B performs an AHT function, and thus illustrates an implantable AHT device. The illustrated device 921B includes controller circuitry 923 and a memory 924. The controller circuitry 923 is capable of being implemented using hardware, software, and combinations of hardware and software. For example, according to various embodiments, the controller circuitry 923 includes a processor to perform instructions embedded in the memory 924 to perform functions associated with NS therapy such as AHT therapy. For example, the illustrated device 921B further includes a transceiver 925 and associated circuitry for use to communicate with a programmer or another external or internal device. Various embodiments have wireless communication capabilities. For example, some transceiver embodiments use a telemetry coil to wirelessly communicate with a programmer or another external or internal device.

The illustrated device 921B further includes baroreceptor stimulation circuitry 926. Various embodiments of the device 921B also includes sensor circuitry 927. One or more leads are able to be connected to the sensor circuitry 927 and baroreceptor stimulation circuitry 926. The baroreceptor stimulation circuitry 926 is used to apply electrical stimulation pulses to desired baroreceptors sites, such as baroreceptor sites in the pulmonary artery, through one or more stimulation electrodes. The sensor circuitry 927 is used to detect and process ANS nerve activity. In various embodiments, the sensor circuitry is further used to detect and process surrogate parameters such as blood pressure, respiration and the like, to determine the ANS activity.

According to various embodiments, the stimulator circuitry 926 includes modules to set any one or any combination of two or more of the following pulse features: the amplitude 928 of the stimulation pulse, the frequency 929 of the stimulation pulse, the burst frequency 930 or duty cycle of the pulse, and the wave morphology 931 of the pulse. Examples of wave morphology include a square wave, triangle wave, sinusoidal wave, and waves with desired harmonic components to mimic white noise such as is indicative of naturally-occurring baroreflex stimulation. Additionally, various controller embodiments are capable of controlling a duration of the stimulation.

Figure 10:
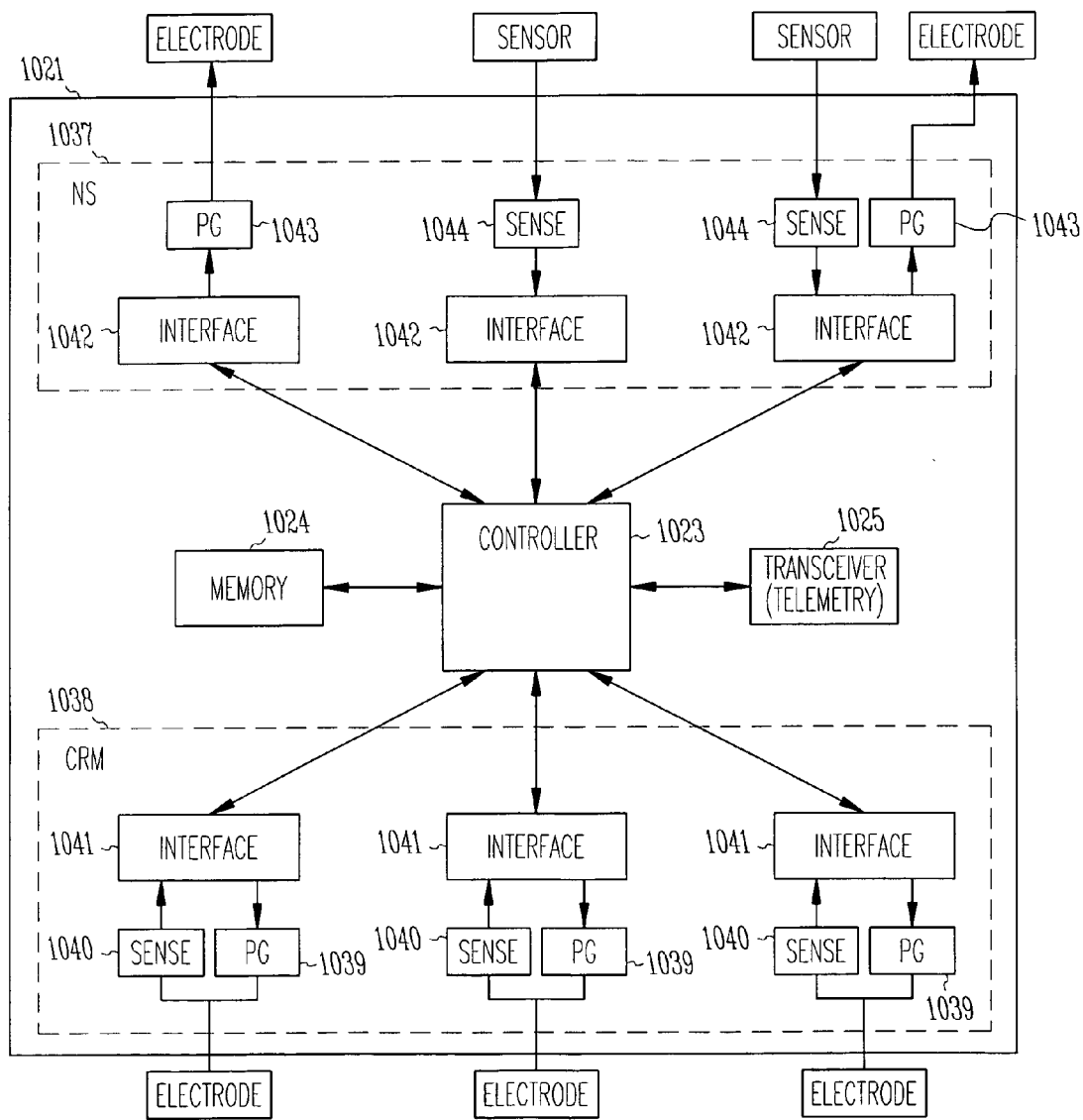
FIG. 10 illustrates an implantable medical device (IMD) such as shown in FIG. 8 having a neural stimulator (NS) component and cardiac rhythm management (CRM) component, according to various embodiments of the present subject matter.

FIG. 10 illustrates an implantable medical device (IMD) such as shown in FIG. 9A having a neural stimulator (NS) component and cardiac rhythm management (CRM) component, according to various embodiments of the present subject matter. Various IMD embodiments do not include a CRM component, as illustrated in FIG. 10. The illustrated device 1021 includes a controller 1023 and a memory 1024. According to various embodiments, the controller 1023 includes hardware, software, or a combination of hardware and software to perform the neural stimulation and CRM functions. Examples of CRM functions include, for example, pacing, defibrillating, and cardiac resynchronization therapy (CRT) functions. For example, the programmed therapy applications discussed in this disclosure are capable of being stored as computer-readable instructions embodied in memory and executed by a processor. According to various embodiments, the controller 1023 includes a processor to execute instructions embedded in memory to perform the baroreceptor stimulation and CRM functions. The illustrated device 1021 further includes a transceiver 1025 and associated circuitry for use to communicate with a programmer or another external or internal device. Various embodiments include a telemetry coil.

The CRM therapy section 1038 includes components, under the control of the controller, to stimulate a heart and/or sense cardiac signals using one or more electrodes. The CRM therapy section includes a pulse generator 1039 for use to provide an electrical signal through an electrode to stimulate a heart, and further includes sense circuitry 1040 to detect and process sensed cardiac signals or otherwise detect pulsatile parameters according to the present subject matter. An interface 1041 is generally illustrated for use to communicate between the controller 1023 and the pulse generator 1039 and sense circuitry 1040. Three electrodes are illustrated as an example for use to provide CRM therapy. However, the present subject matter is not limited to a particular number of electrode sites. One or more electrodes can be positioned on a lead, and one or more leads can be used. Each electrode may include its own pulse generator and sense circuitry. However, the present subject matter is not so limited. The pulse generating and sensing functions can be multiplexed to function with multiple electrodes.

The NS therapy section 1037 includes components, under the control of the controller, to stimulate a baroreceptor and sense ANS parameters associated with nerve activity, and in some embodiments sense surrogates of ANS parameters such as blood pressure and respiration. Examples of NS therapy include, but are not limited to, therapies to treat hypertension, epilepsy, obesity and breathing disorders. Three interfaces 1042 are illustrated for use to provide ANS therapy. However, the present subject matter is not limited to a particular number interfaces, or to any particular stimulating or sensing functions. Pulse generators 1043 are used to provide electrical pulses to an electrode for use to stimulate a baroreceptor site. According to various embodiments, the pulse generator includes circuitry to set, and in some embodiments change, the amplitude of the stimulation pulse, the frequency of the stimulation pulse, the burst frequency of the pulse, and/or the morphology of the pulse such as a square wave, triangle wave, sinusoidal wave, and waves with desired harmonic components to mimic white noise or other signals. Sense circuits 1044 are used to detect and process signals from a sensor, such as a sensor of nerve activity, pulsatile parameters, blood pressure, respiration, and the like. The interfaces 1042 are generally illustrated for use to communicate between the controller 1023 and the pulse generator 1043 and sense circuitry 1044. Each interface, for example, may be used to control a separate lead. Various embodiments of the NS therapy section only include a pulse generator to stimulate baroreceptors. The NS therapy section is capable of providing AHT therapy to treat hypertension, for example.

Embodiments of the NS therapy section modify therapy based on electrophysiological parameters such as heart rate, minute ventilation, atrial activation, ventricular activation, and cardiac events. Embodiments of the CRM therapy section modify therapy based on data received from the NS therapy section, such as mean arterial pressure, systolic and diastolic pressure, and baroreflex stimulation rate.

A system according to these embodiments can be used to augment partially successful treatment strategies. As an example, undesired side effects may limit the use of some pharmaceutical agents. The combination of a system according to these embodiments with reduced drug doses may be particularly beneficial.

According to various embodiments, the lead(s) and the electrode(s) on the leads are physically arranged with respect to the heart in a fashion that enables the electrodes to properly transmit pulses and sense signals from the heart, and with respect to baroreceptors, such as nerve endings and nerve trunks, to stimulate the baroreflex. As there may be a number of leads and a number of electrodes per lead, the configuration can be programmed to use a particular electrode or electrodes. According to various embodiments, the baroreflex is stimulated by stimulating afferent nerve trunks.

Figure 11:
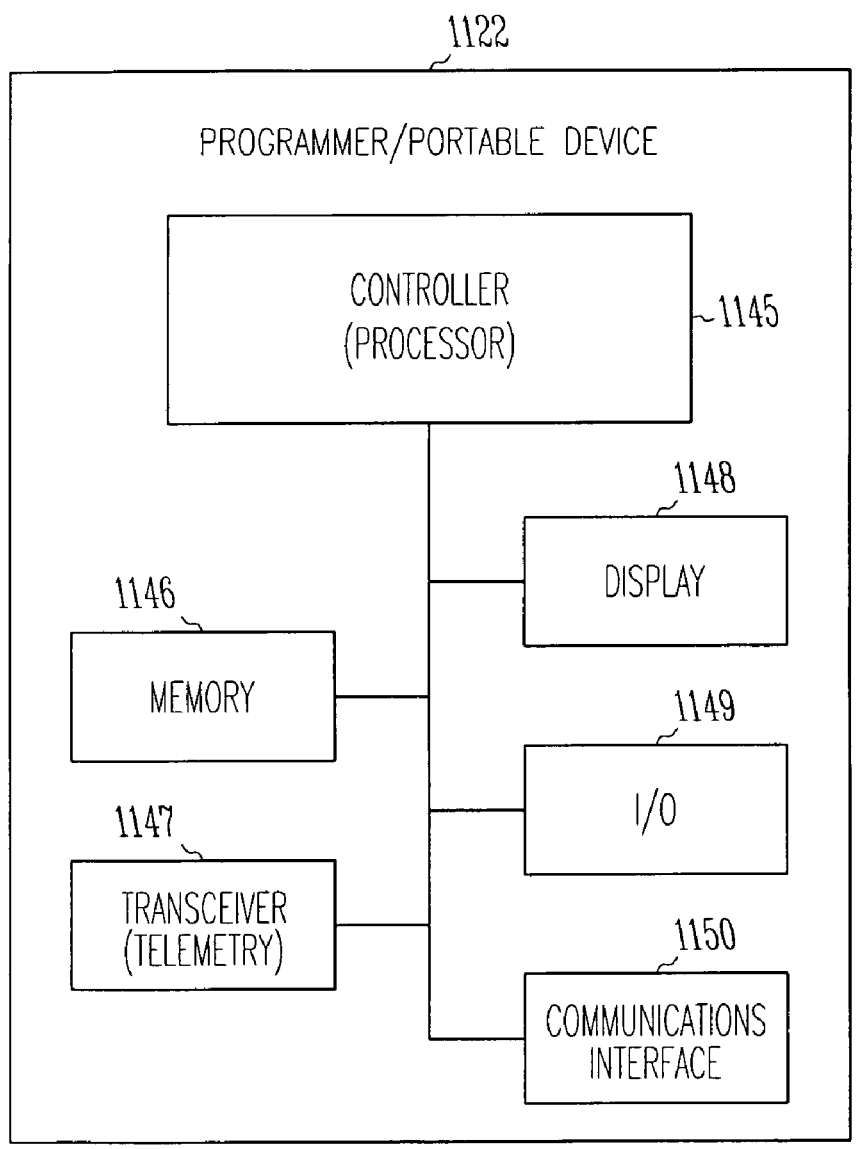
FIG. 11 illustrates a programmer such as illustrated in the system of FIG. 8 or other external device to communicate with the implantable medical device(s), according to various embodiments of the present subject matter.

FIG. 11 illustrates a programmer 1122, such as the programmer 922 illustrated in the systems of FIG. 9, or other external device to communicate with the implantable medical device(s) 921, according to various embodiments of the present subject matter. An example of another external device includes Personal Digital Assistants (PDAs) or personal laptop and desktop computers in an Advanced Patient Management (APM) system. The illustrated device 1122 includes controller circuitry 1145 and a memory 1146. The controller circuitry 1145 is capable of being implemented using hardware, software, and combinations of hardware and software. For example, according to various embodiments, the controller circuitry 1145 includes a processor to perform instructions embedded in the memory 1146 to perform a number of functions, including communicating data and/or programming instructions to the implantable devices. The illustrated device 1122 further includes a transceiver 1147 and associated circuitry for use to communicate with an implantable device. Various embodiments have wireless communication capabilities. For example, various embodiments of the transceiver 1147 and associated circuitry include a telemetry coil for use to wirelessly communicate with an implantable device. The illustrated device 1122 further includes a display 1148, input/output (I/O) devices 1149 such as a keyboard or mouse/pointer, and a communications interface 1150 for use to communicate with other devices, such as over a communication network.

The above-described functions of a system, whether implemented in two separate and distinct implantable devices or integrated as components into one or more implantable devices, includes, but is not limited to, processes for monitoring nerve traffic as part of a closed-loop neural stimulation system to continuously deliver appropriate neural stimulation. Processes can be performed by a processor executing computer-readable instructions embedded in memory, for example.

The present subject matter provides neural stimulation using lead(s) that can be used to provide neural stimulation, and/or to detect and monitor nerve traffic. The lead is adapted to be connected to a device, such as an implantable neural stimulation device or integrated into a CRM device. The device processes the nerve signal with appropriate amplification and filtering for the low amplitude and high noise level associated with the nerve signal. Various embodiments provide a signal processing module that can include a wavelet transformation or other noise reduction algorithm. Recorded nerve traffic is processed with a detection algorithm adapted to identify the features of the signal, such as the pattern and intensity of the nerve traffic. The signal features are used to determine desired neural stimulation parameters, such as duration, frequency and amplitude.

A neural stimulation lead can be placed in a number of appropriate locations. For example, various lead embodiments to stimulate a baroreflex are expandable, and are adapted to be placed in the pulmonary artery in the proximity of a high concentration of baroreceptors. Various lead embodiments are adapted to stimulate nerve endings in cardiac fat pads. Some lead embodiments are transvascular leads placed proximal to a cardiac fat pad. Some lead embodiments place an epicardial lead in a cardiac fat pad. Various lead embodiments include a cuff electrode adapted to be placed around a nerve, such as the aortic, carotid or vagus nerve. Other leads can be placed in other neural stimulation and neural sensing locations to perform baroreflex or other therapy.

The closed-loop neural stimulation can be implemented at a same site or at different sites. In embodiments of a same site implementation, a lead is placed in a baroreceptor field, in a cardiac fat pad, or around or proximate to a nerve trunk (such as the aortic, carotid or vagus nerve). The nerve traffic is detected and monitored with appropriate amplification and filtering characteristics. The pattern and/or intensity of nerve traffic is used to determine neural stimulation parameters, such as duration, frequency, and/or amplitude, at the same site. In embodiments of a different site implementation, two neural leads are placed in different locations, such as one lead in the fat pad and one lead around the vagus nerve, for example. Nerve traffic at one site is used to guide neural stimulation at the second site. Various device embodiments monitor and record autonomic nerve traffic data as part of an APM system.

Various device embodiments include an amplification and filtering circuit adapted to process and monitor nerve traffic. The device includes a signal processing module that includes a noise reduction algorithm such as a wavelet transformation.

Figure 12A:
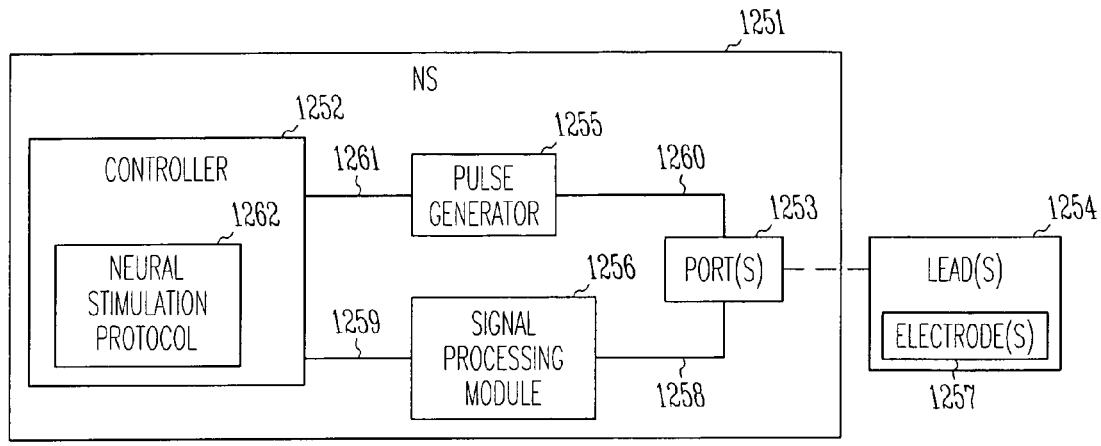
FIGS. 12A-12C illustrate neural stimulators, according to various embodiments of the present subject matter.
Figure 12B:
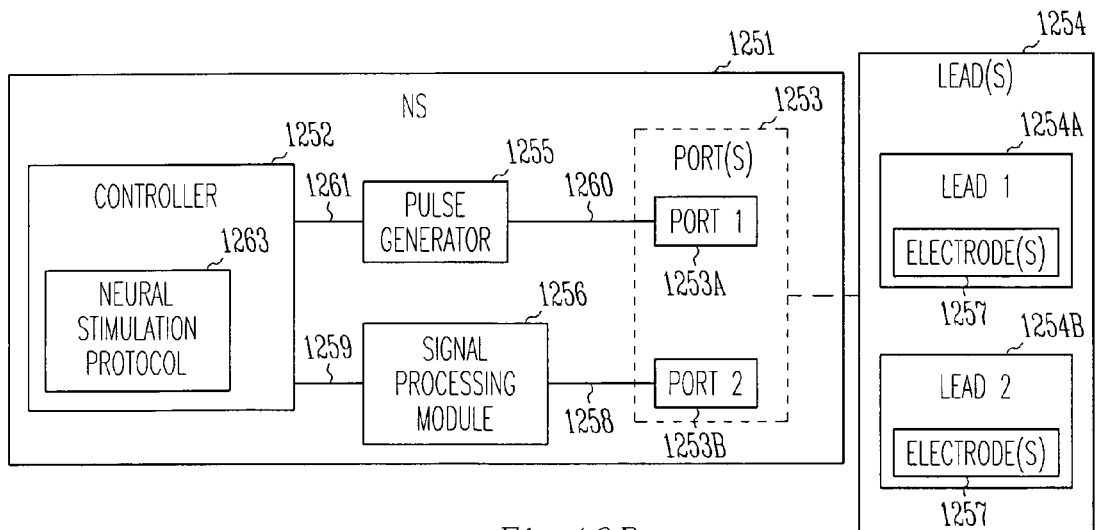
Figure 12C:
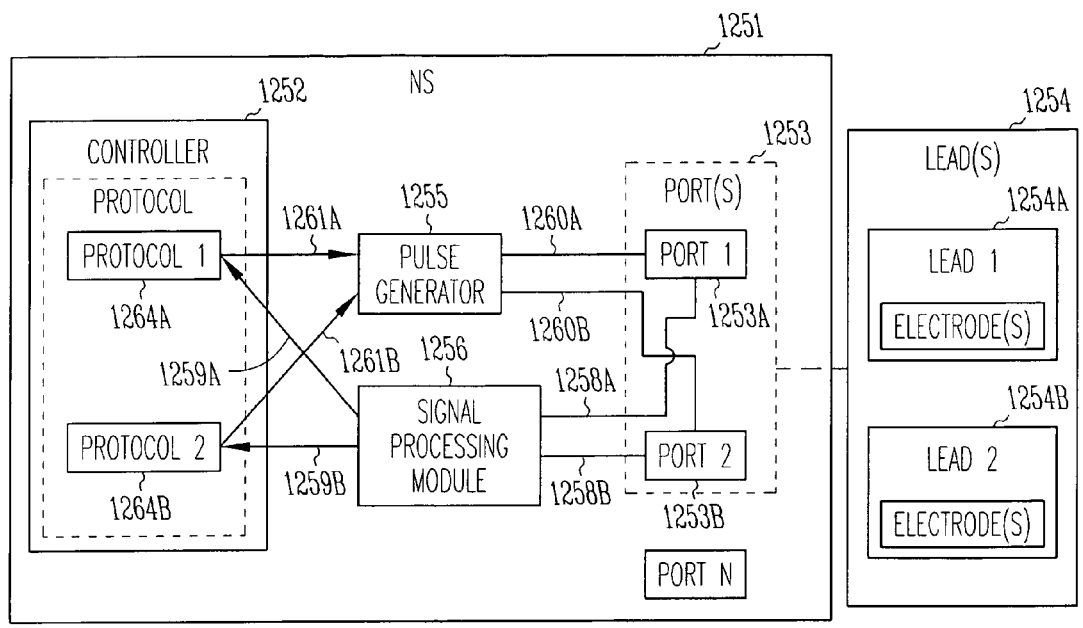

FIGS. 12A-12C illustrate neural stimulators, according to various embodiments of the present subject matter. FIGS. 12A-12C illustrate a few logical arrangements for providing closed-loop neural stimulation based on sensed neural traffic. Other logical arrangements are capable of being implemented, such as are illustrated in FIGS. 16A-16D.

The neural stimulator device 1251 illustrated in FIG. 12A includes a controller 1252, at least one port 1253 to connect at least one lead 1254, a pulse generator 1255 connected to the controller and to the port, and a signal processing module 1256 connected to the controller and to the port. The at least one lead includes at least one electrode 1257 for stimulation and/or sensing. The signal processing module 1256 is adapted to receive and process a nerve traffic signal on path 1258 from the lead into a signal indicative of the nerve traffic on signal path 1259. The pulse generator 1255 is adapted to provide a neural stimulation signal to the lead on signal path 1260 based on a control signal from the controller 1252 on path 1261. The controller is adapted to implement a stimulation protocol 1262, which in conjunction with the pulse generator, provides the neural stimulation signal with desired neural stimulation parameters based on the signal indicative of the nerve traffic received from the lead. For example, the duration, frequency and/or amplitude for the neural stimulation signal are capable of being adjusted based on the signal indicative of nerve traffic. The illustrated device is capable of sensing and stimulating using the same lead. Thus, the closed-loop system can be based on sensed nerve traffic at or near the same site where neural stimulation is applied.

The neural stimulator device 1251 illustrated in FIG. 12B includes a controller 1252, at a first port 1253A to connect a first lead 1254A and a second port 1253B to connect a second lead 1254B, a pulse generator 1255 connected to the controller and to the first port, and a signal processing module 1256 connected to the controller and to the second port. The leads include at least one electrode 1257. The signal processing module 1256 is adapted to receive and process a nerve traffic signal on path 1258 from the second lead 1254B into a signal indicative of the nerve traffic on signal path 1259. The pulse generator 1255 is adapted to provide a neural stimulation signal to the lead on signal path 1260 based on a control signal from the controller 1252 on path 1261. The controller is adapted to implement a stimulation protocol 1263, which in conjunction with the pulse generator, provides the neural stimulation signal with desired neural stimulation parameters to the first lead based on the signal indicative of the nerve traffic received from the second lead. Thus, nerve traffic at one site is capable of being used to guide neural stimulation at another site. For example, the duration, frequency and /or amplitude for the neural stimulation signal are capable of being adjusted based on the signal indicative of nerve traffic.

The neural stimulator device 1251 illustrated in FIG. 12C includes a controller 1252, a first port 1253A to connect a first lead 1254A and a second port 1253B to connect a second lead 1254B, a pulse generator 1255 connected to the controller via path 1261A and 1261B and operably connected to the first and second ports via paths 1258A and 1258B to perform a desired stimulation, and a signal processing module 1256 connected to the controller 1252 via path 1259A and 1259B and operably connected to the first and second ports to provide desired sensing. The leads include at least one electrode. The signal processing module 1256 is adapted to receive and process a nerve traffic signal on path 1258A from the first lead and on path 1258B from the second lead into a signals indicative of the nerve traffic sensed by the first and second leads, respectively. The pulse generator 1255 is adapted to provide a neural stimulation signal to the first lead on signal path 1260A based on a control signal from the controller 1252 on path 1261A, and to the second lead on signal path 1260B based on a control signal from the controller 1252 on path 1261B. The controller is adapted to implement a stimulation protocol or protocols 1264A and 1264B, which in conjunction with the pulse generator, provides the neural stimulation signal with desired neural stimulation parameters to the first lead based on the signal indicative of the nerve traffic received from the second lead, and further provides the neural stimulation with desired neural stimulation parameters to the second lead based on the signal indicative of the nerve traffic received from the first lead. For example, the duration, frequency and /or amplitude for the neural stimulation signal are capable of being adjusted based on the signal indicative of nerve traffic. As illustrated in the FIG. 12C, additional ports (Port N) can be included for use in sensing and/or stimulation.

According to various embodiments, the signal processing module is adapted to provide a signal or signals indicative of a nerve traffic pattern and/or nerve traffic intensity as an indication of the nerve traffic. According to various embodiments, the signal processing module is adapted to implement noise reduction algorithm, such as a wavelet transformation, to identify features of a nerve traffic signal that is characterized by a low amplitude and high noise level. According to various embodiments, the signal processing module includes an amplifier, such as an amplifier with a gain within a range of approximately 1,000 to approximately 99,000. According to various embodiments, the signal processing module includes a bandpass filter, such as a filter to pass frequencies in a range from approximately 30 Hz to approximately 3,000 Hz.

Figure 13:
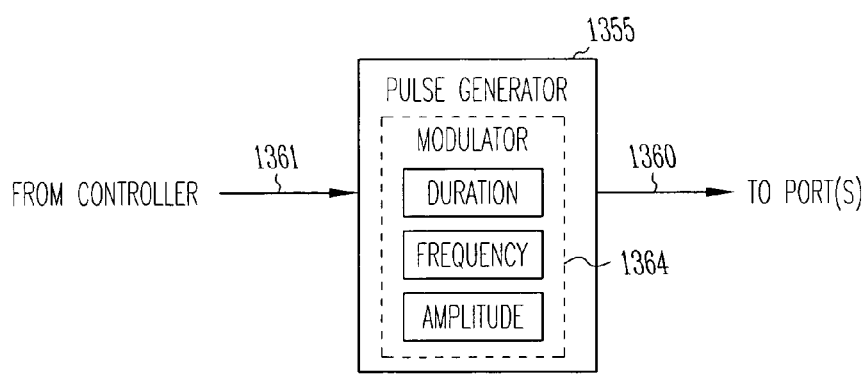
FIG. 13 illustrates a pulse generator, such as shown in the neural stimulators of FIGS. 12A-12C, according to various embodiments of the present subject matter.

FIG. 13 illustrates a pulse generator, such as shown in the neural stimulators of FIGS. 12A-12C, according to various embodiments of the present subject matter. The illustrated pulse generator 1355 is adapted to receive a control signal via path 1361 from a controller and to provide a neural stimulation signal via path 1360 to lead(s) via port(s). The illustrated pulse generator includes a modulator 1364 that is responsive to the control signal from the controller to change one or more parameters of the stimulation signal such as the duration, frequency and/or amplitude of the stimulation signal.

Figure 14:
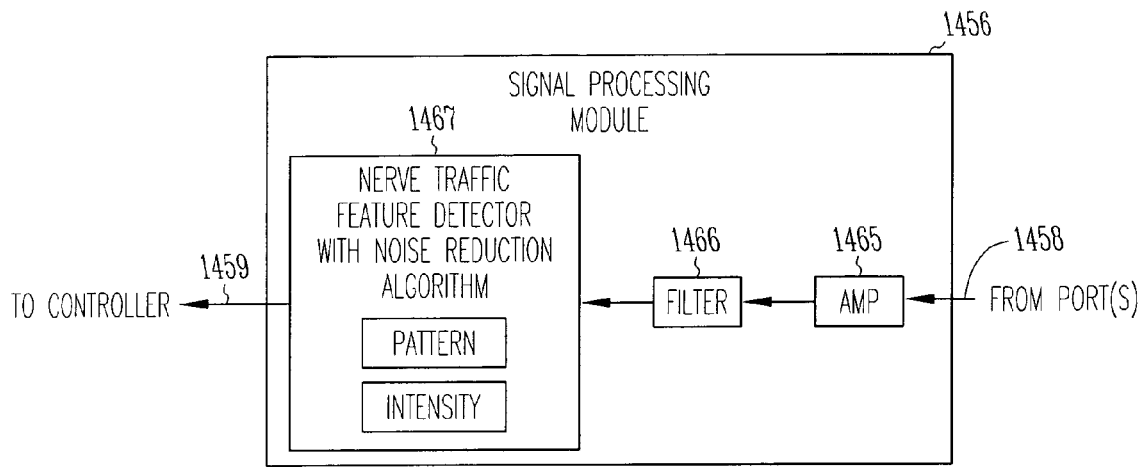
FIG. 14 illustrates a signal processing module, such as shown in the neural stimulators of FIGS. 12A-12C, according to various embodiments of the present subject matter.

FIG. 14 illustrates a signal processing module, such as shown in the neural stimulators of FIGS. 12A-12C, according to various embodiments of the present subject matter. The illustrated signal processing module 1456 is adapted to receive a nerve traffic signal via path 1458 and port(s) from lead(s) and to provide a signal indicative of the nerve traffic via path 1459 to the controller. Various embodiments include an amplifier 1465 and filter 1466 adapted to process the nerve activity into a signal conditioned for discrimination or other processing. Various amplifier embodiments provide a gain within a range of approximately 1,000 to 99,000. Various filter embodiments pass frequencies in a range from approximately 30 Hz to approximately 3,000 Hz. The illustrated signal processing module further includes a nerve traffic feature detector 1467, also referred to as a discriminator, to process the amplified and filtered signal to provide a signal indicative of the nerve traffic to the controller. Various embodiments implement a noise reduction algorithm, such as a wavelet transformation, for use in discriminating the signal. Various embodiments of the nerve traffic feature detector discriminate a noise traffic pattern feature and/or a noise traffic intensity feature; and send these signals to the controller for use to guide the neural stimulation.

Figure 15:
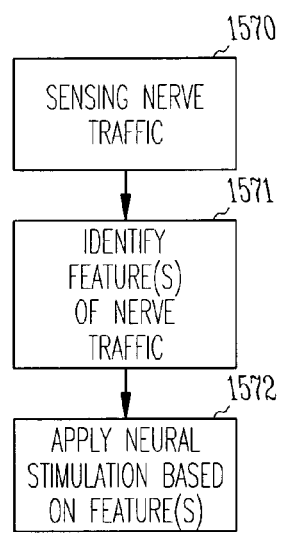
FIG. 15 illustrates a method for closed-loop stimulation, according to various embodiments of the present subject matter.

FIG. 15 illustrates method for closed-loop stimulation, according to various embodiments of the present subject matter. At 1570, nerve traffic is sensed. At 1571, one or more features of the nerve traffic is identified. Various embodiments for identifying the feature(s) of the nerve traffic include implementing a noise reduction algorithm, such as a wavelet transformation. Examples of identified features include the pattern and intensity of the nerve traffic. In various embodiments, discriminating the signal to identify features of the nerve traffic signal includes rectifying and applying a threshold to the nerve traffic signal. In various embodiments, the discriminated signal is integrated using, for example, and R-C Integrator 0.1 sec, to obtain a value for the nerve traffic activity over a 100 millisecond period of time. At 1572, neural stimulation is applied based on one or more features identified at 1571. In various embodiments, a controller implements a stimulation protocol to change at least one parameter, such as duration, amplitude and/or frequency, of the stimulation signal.

FIGS. 16A-16D illustrate various closed-loop control systems implemented by various neural stimulation device embodiments. The neural stimulation device embodiment 1651A illustrated in FIG. 16A neural stimulates and senses nerve traffic at the same site. For example, a nerve, nerve ending or other site is stimulated during a first time period, and is sensed during a second time period. The sensed nerve traffic is used to adjust subsequent neural stimulations.

Figure 16A:
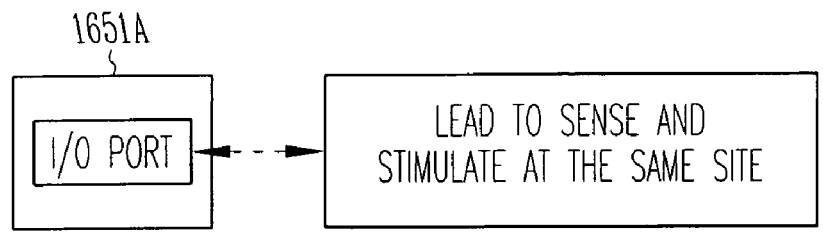
Figure 16B:
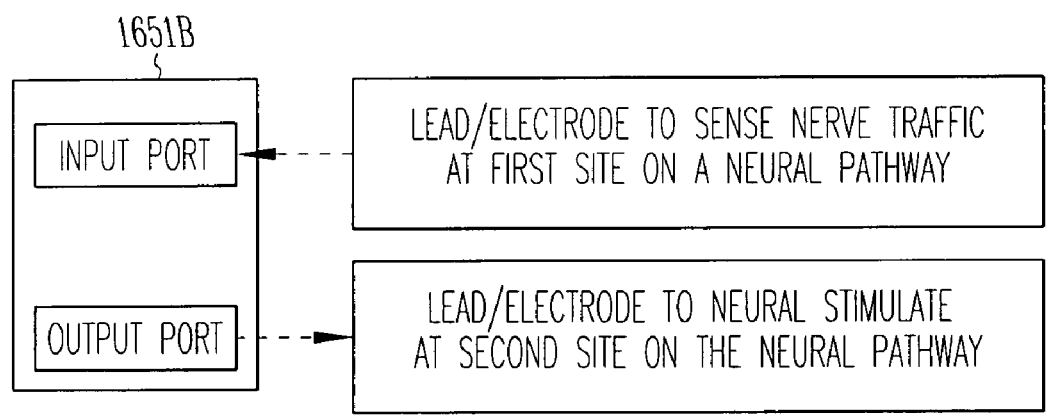

The neural stimulation device embodiment 1651B illustrated in FIG. 16B neural stimulates a first site (e.g. nerve ending or nerve) on a neural pathway, and senses nerve traffic at a second site (e.g. nerve ending or nerve) on the same neural pathway. Thus, a vagus nerve trunk, by way of example and not by way of limitation, is stimulated and the resulting nerve traffic on the vagus nerve trunk is capable of being simultaneously sensed to provide feedback to adjust the neural stimulation.

The neural stimulation device embodiment 1651C illustrated in FIG. 16C senses nerve traffic at an afferent nerve site, and neural stimulates at an efferent nerve site. In this embodiment, the neural stimulation device bypasses the central nervous system (CNS). In a healthy nervous system, the CNS receives nerve signals from afferent nerves and appropriately responds by sending appropriate nerve signals to effectors over efferent nerves. Such a system can be used to treat dysautomia, a condition where the autonomic nervous system (ANS) is dysfunctional, by bypassing the CNS by sensing afferent nerves and stimulating efferent nerves. Dysautomia includes Postural Orthostatic Tachycardia Syndrome (POTS), Neurocardiogenic Syncope (NCS), Pure Autonomic Failure (PAF) and Multiple System Atrophy (MSA). Thus, such a system bypasses the CNS physiologic feedback for certain neural functions to override dysfunctions of the autonomic nervous system.

The neural stimulation device embodiment 1651D illustrated in FIG. 16D senses nerve traffic at a first site on a first neural pathway, and neural stimulates at a second site on a second neural pathway. Thus, by way of example and not by way of limitation, nerve activity associated with baroreceptors can be used to provide an indication of blood pressure, and heart rate can be appropriately controlled with appropriate neural stimulation of the SA cardiac fat pad.

One of ordinary skill in the art will understand that, the modules and other circuitry shown and described herein can be implemented using software, hardware, and combinations of software and hardware. As such, the term module is intended to encompass software implementations, hardware implementations, and software and hardware implementations.

The methods illustrated in this disclosure are not intended to be exclusive of other methods within the scope of the present subject matter. Those of ordinary skill in the art will understand, upon reading and comprehending this disclosure, other methods within the scope of the present subject matter. The above-identified embodiments, and portions of the illustrated embodiments, are not necessarily mutually exclusive. These embodiments, or portions thereof, can be combined. For example, various embodiments combine two or more of the illustrated processes. Two or more sensed parameters can be combined into a composite parameter used to provide a desired neural stimulation (NS) or anti-hypertension (AHT) therapy. In various embodiments, the methods provided above are implemented as a computer data signal embodied in a carrier wave or propagated signal, that represents a sequence of instructions which, when executed by a processor cause the processor to perform the respective method. In various embodiments, methods provided above are implemented as a set of instructions contained on a computer-accessible medium capable of directing a processor to perform the respective method. In various embodiments, the medium is a magnetic medium, an electronic medium, or an optical medium.

Although specific embodiments have been illustrated and described herein, it will be appreciated by those of ordinary skill in the art that any arrangement which is calculated to achieve the same purpose may be substituted for the specific embodiment shown. This application is intended to cover adaptations or variations of the present subject matter. It is to be understood that the above description is intended to be illustrative, and not restrictive. Combinations of the above embodiments as well as combinations of portions of the above embodiments in other embodiments will be apparent to those of skill in the art upon reviewing the above description. The scope of the present subject matter should be determined with reference to the appended claims, along with the full scope of equivalents to which such claims are entitled.

What is claimed is:

1. A device for delivering a closed-loop neural stimulation therapy with neural response feedback to a desired neural target in an autonomic nervous system to elicit a desired neural response, comprising:
   a port adapted to connect a lead;
   a memory including instructions stored therein to implement the closed-loop neural stimulation therapy, wherein implementation of the neural stimulation therapy causes a sympathetic or parasympathetic neural response, and the instructions to implement the neural stimulation therapy include instructions to use a detected neural response to the neural stimulation therapy as feedback for the closed-loop neural stimulation therapy, and to modify the neural stimulation therapy based on the detected neural response to provide the desired neural response to the neural stimulation therapy;
   a pulse generator connected to the port and adapted to provide a neural stimulation signal to the lead, wherein the pulse generator and the lead are adapted to cooperate to stimulate the desired neural target for the neural stimulation therapy using the neural stimulation signal;
   a signal processing module connected to the port and adapted to receive and process a nerve traffic signal from the lead into a signal indicative of the detected neural response to stimulating the neural target; and
   a controller connected to the pulse generator and the signal processing module, wherein the controller is configured to execute the instructions in the memory to implement the neural stimulation therapy using the detected neural response as feedback for the neural stimulation therapy, wherein the detected neural response is used to adjust at least one stimulation parameter of the neural stimulation signal based on the detected neural response to provide the desired neural response to the neural stimulation therapy.

2. The device of claim 1, wherein the signal indicative of the detected neural response includes a signal indicative of a nerve traffic pattern.

3. The device of claim 1, wherein the signal indicative of the detected neural response includes a signal indicative of nerve traffic intensity.

4. The device of claim 1, wherein the signal indicative of the detected neural response includes a signal indicative of a nerve traffic pattern and nerve traffic intensity.

5. The device of claim 1, wherein signal processing module is adapted to implement a noise reduction algorithm to identify features of the nerve traffic signal.

6. The device of claim 5, wherein the noise reduction algorithm includes a wavelet transformation.

7. The device of claim 5, wherein the noise reduction algorithm identifies a pattern and an intensity of the nerve traffic signal.

8. The device of claim 1, wherein the signal processing module includes an amplifier and a filter adapted to process and monitor nerve traffic.

9. The device of claim 8, wherein the amplifier includes an amplifier with a gain of approximately 1,000 to approximately 99,000.

10. The device of claim 9, wherein the filter includes a bandpass filter to pass frequencies in a range from approximately 30 Hz to approximately 3,000 Hz.

11. The device of claim 1, wherein the controller is adapted to implement the neural stimulation protocol to adjust a duration for the neural stimulation signal.

12. The device of claim 1, wherein the controller is adapted to implement the neural stimulation protocol to adjust a frequency for the neural stimulation signal.

13. The device of claim 1, wherein the controller is adapted to implement the neural stimulation protocol to adjust an amplitude for the neural stimulation signal.

14. The device of claim 1, wherein the controller is adapted to implement the neural stimulation protocol to adjust two or more parameters of the neural stimulation signal, the two or more parameters being selected from a parameter group consisting of a duration of the neural stimulation signal, a frequency of the neural stimulation signal, and an amplitude of the neural stimulation signal.

15. The device of claim 1, wherein the controller is adapted to sense the nerve traffic signal at a first site, and then apply the neural stimulation signal at the first site.

16. The device of claim 1, wherein the controller is adapted to sense the nerve traffic signal at a first site on a neural pathway and apply the neural stimulation signal at a second site on the neural pathway.

17. The device of claim 16, wherein the controller is adapted to simultaneously sense the nerve traffic signal and apply the neural stimulation signal.

18. The device of claim 1, wherein the neural stimulation therapy includes a neural stimulation therapy for a cardiovascular condition.

19. The device of claim 1, wherein the neural stimulation therapy includes an anti-hypertension therapy.

20. The device of claim 1, wherein the neural stimulation therapy includes a heart failure therapy.

21. A device for delivering a closed-loop neural stimulation therapy with neural response feedback to a desired neural target in an autonomic nervous system to elicit a desired neural response, comprising:
   at least a first port adapted to connect a first lead and a second port adapted to connect a second lead;
   a memory including instructions stored therein to implement the closed-loop neural stimulation therapy, wherein implementation of the neural stimulation therapy causes the sympathetic or parasympathetic neural response, and the instructions to implement the neural stimulation therapy include instructions to use a detected neural response to the neural stimulation therapy as feedback for the closed-loop neural stimulation therapy, and to modify the neural stimulation therapy based on the detected neural response to provide the desired neural response to the neural stimulation therapy;
   a pulse generator connected to at least the first port and adapted to provide a first neural stimulation signal on the first lead, wherein and the pulse generator and the first lead are adapted to cooperate to stimulate the desired neural target for the neural stimulation therapy using the first neural stimulation signal;
   a signal processing module connected to at least the second port and adapted to receive and process a nerve traffic signal from the second lead into a first signal indicative of a detected neural response to stimulating the neural target at an electrode of the second lead; and
   a controller connected to the pulse generator and the signal processing module, wherein the controller is configured to execute the instructions in the memory to implement the neural stimulation therapy using the detected neural response as feedback for the neural stimulation therapy, wherein the detected neural response is used to adjust at least one stimulation parameter of the first neural stimulation signal based on the detected neural response to provide the desired neural response to the neural stimulation therapy.

22. The device of claim 21, wherein:
the pulse generator is further connected to the second port and adapted to provide a second neural stimulation on the second lead;
the signal processing module is further connected to the first port and adapted to receive and process a nerve traffic signal from the first lead into a second signal indicative of the nerve traffic at an electrode of the second lead; and
the stimulation protocol to be implemented by the controller is adapted to provide the second neural stimulation signal with desired neural stimulation parameters based on the second signal indicative of the nerve traffic.

23. The device of claim 22, wherein the signal indicative of the nerve traffic includes a signal indicative of a nerve traffic pattern.

24. The device of claim 22, wherein the first and second signals include a signal indicative of nerve traffic intensity.

25. The device of claim 22, wherein the first and second signals include a signal indicative of a nerve traffic pattern and nerve traffic intensity.

26. The device of claim 21, wherein signal processing module is adapted to implement a noise reduction algorithm to identify features of the nerve traffic signal.

27. The device of claim 26, wherein the noise reduction algorithm includes a wavelet transformation.

28. The device of claim 26, wherein the signal processing module includes an amplifier with a gain of approximately 1,000 to approximately 99,000, and a bandpass filter to pass signals in a range from approximately 30 Hz to approximately 3,000 Hz.

29. The device of claim 21, wherein the nerve traffic includes nerve traffic at an afferent nerve site, and the controller is adapted to provide the first neural stimulation signal with desired parameters for an efferent nerve site based on the first signal indicative of the nerve traffic at the afferent nerve site.

30. The device of claim 21, wherein the nerve traffic includes nerve traffic on a first neural pathway, and the controller is adapted to provide the first neural stimulation signal with desired parameters for a second neural pathway based on the first signal indicative of the nerve traffic at the first neural pathway.

31. The device of claim 21, wherein the neural stimulation therapy includes a neural stimulation therapy for a cardiovascular condition.

32. The device of claim 21, wherein the neural stimulation therapy includes an anti-hypertension therapy.

33. The device of claim 21, wherein the neural stimulation therapy includes a heart failure therapy.

* * * * *